US009150929B2

(12) United States Patent
Xing et al.

(10) Patent No.: US 9,150,929 B2
(45) Date of Patent: Oct. 6, 2015

(54) ANAPLASTIC THYROID CANCERS HARBOR NOVEL ONCOGENIC MUTATIONS OF THE ALK GENE

(75) Inventors: Michael Mingzhao Xing, Clarksville, MD (US); Murugan Avaniyapuram Kannan, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 101 days.

(21) Appl. No.: 14/117,898

(22) PCT Filed: May 7, 2012

(86) PCT No.: PCT/US2012/038285

§ 371 (c)(1),
(2), (4) Date: Jan. 17, 2014

(87) PCT Pub. No.: WO2012/158880

PCT Pub. Date: Nov. 22, 2012

(65) Prior Publication Data

US 2014/0128432 A1 May 8, 2014

Related U.S. Application Data

(60) Provisional application No. 61/487,151, filed on May 17, 2011.

(51) Int. Cl.

| | |
|---|---|
| ***A61K 31/4545*** | (2006.01) |
| ***A61K 45/06*** | (2006.01) |
| ***C12Q 1/68*** | (2006.01) |
| ***A61K 31/4155*** | (2006.01) |

(52) U.S. Cl.

CPC .......... *C12Q 1/6886* (2013.01); *A61K 31/4155* (2013.01); *A61K 31/4545* (2013.01); *A61K 45/06* (2013.01)

(58) Field of Classification Search

CPC ... A61K 31/4545; A61K 45/06; C12Q 1/6886
USPC .......................................... 514/318; 435/6.11
See application file for complete search history.

(56) References Cited

U.S. PATENT DOCUMENTS

| | | | |
|---|---|---|---|
| 2009/0156475 A1 | 6/2009 | Rikova et al. | |
| 2011/0020365 A1 | 1/2011 | Maris et al. | |

OTHER PUBLICATIONS

Wu, et al., "Uncommon mutation, but common amplifications of the PIK3CA gene in thyroid tumors", The Journal of Clinical Endocrinology & Metabolism, (2005) vol. 90, No. 8, pp. 4688-4693, ISSN 1945-7197.

Murugan, et al., "Anaplastic thyroid cancers harbor novel oncogenic mutations of the ALK gene", Cancer Research, May 19, 2011, vol. 71, No. 13, pp. 4403-4411, ISSN 1538-7445.

*Primary Examiner* — Raymond Henley, III

(74) *Attorney, Agent, or Firm* — Johns Hopkins Technology Transfer

(57) ABSTRACT

The present invention relates to diagnostic, therapeutic and prognostic methods for thyroid cancers. In one embodiment, the present invention provides a method for treating a an anaplastic thyroid cancer (ATC) patient comprising the step of administering to the patient an effective amount of an anaplastic lymphoma kinase (ALK) inhibitor. In another embodiment, a method for diagnosing ATC in patient comprises the step of performing an assay on a biological sample from the patient to identify the presence or absence of a C3592T and/or a G3602A mutation in exon 23 of the ALK gene according to SEQ ID NO:6, wherein the presence of either of both of the mutations correlates with a diagnosis of ATC in the patient.

28 Claims, 5 Drawing Sheets

SEQUENCE LISTING

```
<160> NUMBER OF SEQ ID NOS: 9

<210> SEQ ID NO 1
<211> LENGTH: 27
<212> TYPE: DNA
<213> ORGANISM: Artificial Sequence
<220> FEATURE:
<223> OTHER INFORMATION: Sense primer for ALK mutant L1198F

<400> SEQUENCE: 1

catcctgctg gagttcatgg cgggggg                                     27


<210> SEQ ID NO 2
<211> LENGTH: 27
<212> TYPE: DNA
<213> ORGANISM: Artificial Sequence
<220> FEATURE:
<223> OTHER INFORMATION: Antisense primer for ALK mutant L1198F

<400> SEQUENCE: 2

ccccccgcca tgaactccag caggatg                                     27


<210> SEQ ID NO 3
<211> LENGTH: 27
<212> TYPE: DNA
<213> ORGANISM: Artificial Sequence
<220> FEATURE:
<223> OTHER INFORMATION: Sense primer for ALK mutant G1201E

<400> SEQUENCE: 3

gagctcatgg cggagggaga cctcaag                                     27


<210> SEQ ID NO 4
<211> LENGTH: 27
<212> TYPE: DNA
<213> ORGANISM: Artificial Sequence
<220> FEATURE:
<223> OTHER INFORMATION: Antisense primer for ALK mutant G1201E

<400> SEQUENCE: 4

cttgaggtct ccctccgcca tgagctc                                     27


<210> SEQ ID NO 5
<211> LENGTH: 20
```

<212> TYPE: DNA
<213> ORGANISM: Artificial Sequence
<220> FEATURE:
<223> OTHER INFORMATION: Vector sequencing primer for confirming mutations

<400> SEQUENCE: 5
tctcgctgtg gtgacctctg 20

<210> SEQ ID NO 6
<211> LENGTH: 6222
<212> TYPE: DNA
<213> ORGANISM: Homo sapiens
<220> FEATURE:
<221> NAME/KEY: misc_feature
<222> LOCATION: (1)..(6222)
<223> OTHER INFORMATION: Nucleic acid sequence for human ALK

<400> SEQUENCE: 6
gggggcggca gcggtggtag cagctggtac ctcccgccgc ctctgttcgg agggtcgcgg 60
ggcaccgagg tgctttccgg ccgccctctg gtcggccacc caaagccgcg ggcgctgatg 120
atgggtgagg agggggcggc aagatttcgg gcgcccctgc cctgaacgcc ctcagctgct 180
gccgccgggg ccgctccagt gcctgcgaac tctgaggagc cgaggcgccg gtgagagcaa 240
ggacgctgca aacttgcgca gcgcgggggc tgggattcac gcccagaagt tcagcaggca 300
gacagtccga agccttcccg cagcggagag atagcttgag ggtgcgcaag acggcagcct 360
ccgccctcgg ttcccgccca gaccgggcag aagagcttgg aggagccaaa aggaacgcaa 420
aaggcggcca ggacagcgtg cagcagctgg gagccgccgt tctcagcctt aaaagttgca 480
gagattggag gctgccccga gaggggacag accccagctc cgactgcggg gggcaggaga 540
ggacggtacc caactgccac ctcccttcaa ccatagtagt tcctctgtac cgagcgcagc 600
gagctacaga cgggggcgcg gcactcggcg cggagagcgg gaggctcaag gtcccagcca 660
gtgagcccag tgtgcttgag tgtctctgga ctcgcccctg agcttccagg tctgtttcat 720
ttagactcct gctcgcctcc gtgcagttgg gggaaagcaa gagacttgcg cgcacgcaca 780
gtcctctgga gatcaggtgg aaggagccgc tgggtaccaa ggactgttca gagcctcttc 840
ccatctcggg gagagcgaag ggtgaggctg ggcccggaga gcagtgtaaa cggcctcctc 900
cggcgggatg ggagccatcg ggctcctgtg gctcctgccg ctgctgcttt ccacggcagc 960
tgtgggctcc gggatgggga ccggccagcg cgcgggctcc ccagctgcgg ggccgccgct 1020
gcagccccgg gagccactca gctactcgcg cctgcagagg aagagtctgg cagttgactt 1080
cgtggtgccc tcgctcttcc gtgtctacgc ccgggaccta ctgctgccac catcctcctc 1140
ggagctgaag gctggcaggc ccgaggcccg cggctcgcta gctctggact gcgccccgct 1200
gctcaggttg ctggggccgg cgccgggggt ctcctggacc gccggttcac cagccccggc 1260
agaggcccgg acgctgtcca gggtgctgaa gggcggctcc gtgcgcaagc tccggcgtgc 1320
caagcagttg gtgctggagc tgggcgagga ggcgatcttg gagggttgcg tcgggccccc 1380
cggggaggcg gctgtggggc tgctccagtt caatctcagc gagctgttca gttggtggat 1440
tcgccaaggc gaagggcgac tgaggatccg cctgatgccc gagaagaagg cgtcggaagt 1500
gggcagagag ggaaggctgt ccgcggcaat tcgcgcctcc cagccccgcc ttctcttcca 1560
gatcttcggg actggtcata gctccttgga atcaccaaca aacatgcctt ctccttctcc 1620
tgattatttt acatggaatc tcacctggat aatgaaagac tccttccctt tcctgtctca 1680
tcgcagccga tatggtctgg agtgcagctt tgacttcccc tgtgagctgg agtattcccc 1740

-continued

```
tccactgcat gacctcagga accagagctg gtcctggcgc cgcatcccct ccgaggaggc   1800
ctcccagatg gacttgctgg atgggcctgg ggcagagcgt tctaaggaga tgcccagagg   1860
ctcctttctc cttctcaaca cctcagctga ctccaagcac accatcctga gtccgtggat   1920
gaggagcagc agtgagcact gcacactggc cgtctcggtg cacaggcacc tgcagccctc   1980
tggaaggtac attgcccagc tgctgcccca caacgaggct gcaagagaga tcctcctgat   2040
gcccactcca gggaagcatg gttggacagt gctccaggga agaatcgggc gtccagacaa   2100
cccatttcga gtggccctgg aatacatctc cagtggaaac cgcagcttgt ctgcagtgga   2160
cttctttgcc ctgaagaact gcagtgaagg aacatcccca ggctccaaga tggccctgca   2220
gagctccttc acttgttgga atgggacagt cctccagctt gggcaggcct gtgacttcca   2280
ccaggactgt gcccagggag aagatgagag ccagatgtgc cggaaactgc ctgtgggttt   2340
ttactgcaac tttgaagatg gcttctgtgg ctggacccaa ggcacactgt caccccacac   2400
tcctcaatgg caggtcagga ccctaaagga tgcccggttc caggaccacc aagaccatgc   2460
tctattgctc agtaccactg atgtccccgc ttctgaaagt gctacagtga ccagtgctac   2520
gtttcctgca ccgatcaaga gctctccatg tgagctccga atgtcctggc tcattcgtgg   2580
agtcttgagg ggaaacgtgt ccttggtgct agtggagaac aaaaccggga aggagcaagg   2640
caggatggtc tggcatgtcg ccgcctatga aggcttgagc ctgtggcagt ggatggtgtt   2700
gcctctcctc gatgtgtctg acaggttctg gctgcagatg gtcgcatggt ggggacaagg   2760
atccagagcc atcgtggctt ttgacaatat ctccatcagc ctggactgct acctcaccat   2820
tagcggagag gacaagatcc tgcagaatac agcacccaaa tcaagaaacc tgtttgagag   2880
aaacccaaac aaggagctga aacccgggga aaattcacca agacagaccc ccatctttga   2940
ccctacagtt cattggctgt tcaccacatg tggggccagc gggccccatg gccccaccca   3000
ggcacagtgc aacaacgcct accagaactc caacctgagc gtggaggtgg ggagcgaggg   3060
ccccctgaaa ggcatccaga tctggaaggt gccagccacc gacacctaca gcatctcggg   3120
ctacggagct gctggcggga aaggcgggaa gaacaccatg atgcggtccc acggcgtgtc   3180
tgtgctgggc atcttcaacc tggagaagga tgacatgctg tacatcctgg ttgggcagca   3240
gggagaggac gcctgcccca gtacaaacca gttaatccag aaagtctgca ttggagagaa   3300
caatgtgata gaagaagaaa tccgtgtgaa cagaagcgtg catgagtggg caggaggcgg   3360
aggaggaggg ggtggagcca cctacgtatt taagatgaag gatggagtgc cggtgcccct   3420
gatcattgca gccggaggtg gtggcagggc ctacggggcc aagacagaca cgttccaccc   3480
agagagactg gagaataact cctcggttct agggctaaac ggcaattccg gagccgcagg   3540
tggtggaggt ggctggaatg ataacacttc cttgctctgg gccggaaaat ctttgcagga   3600
gggtgccacc ggaggacatt cctgccccca ggccatgaag aagtgggggt gggagacaag   3660
agggggtttc ggagggggtg gagggggtg ctcctcaggt ggaggaggcg gaggatatat   3720
aggcggcaat gcagcctcaa acaatgaccc cgaaatggat ggggaagatg gggtttcctt   3780
catcagtcca ctgggcatcc tgtacacccc agctttaaaa gtgatggaag gccacgggga   3840
agtgaatatt aagcattatc taaactgcag tcactgtgag gtagacgaat gtcacatgga   3900
ccctgaaagc cacaaggtca tctgcttctg tgaccacggg acggtgctgg ctgaggatgg   3960
cgtctcctgc attgtgtcac ccaccccgga gccacacctg ccactctcgc tgatcctctc   4020
tgtggtgacc tctgccctcg tggccgccct ggtcctggct ttctccggca tcatgattgt   4080
```

-continued

```
gtaccgccgg aagcaccagg agctgcaagc catgcagatg gagctgcaga gccctgagta   4140

caagctgagc aagctccgca cctcgaccat catgaccgac tacaacccca actactgctt   4200

tgctggcaag acctcctcca tcagtgacct gaaggaggtg ccgcggaaaa acatcaccct   4260

cattcggggt ctgggccatg gcgcctttgg ggaggtgtat gaaggccagg tgtccggaat   4320

gcccaacgac ccaagccccc tgcaagtggc tgtgaagacg ctgcctgaag tgtgctctga   4380

acaggacgaa ctggatttcc tcatggaagc cctgatcatc agcaaattca accaccagaa   4440

cattgttcgc tgcattgggg tgagcctgca atccctgccc cggttcatcc tgctggagct   4500

catggcgggg ggagacctca agtccttcct ccgagagacc cgccctcgcc cgagccagcc   4560

ctcctccctg gccatgctgg accttctgca cgtggctcgg gacattgcct gtggctgtca   4620

gtatttggag gaaaaccact tcatccaccg agacattgct gccagaaact gcctcttgac   4680

ctgtccaggc cctggaagag tggccaagat tggagacttc gggatggccc gagacatcta   4740

cagggcgagc tactatagaa agggaggctg tgccatgctg ccagttaagt ggatgccccc   4800

agaggccttc atggaaggaa tattcacttc taaaacagac acatggtcct ttggagtgct   4860

gctatgggaa atcttttctc ttggatatat gccatacccc agcaaaagca accaggaagt   4920

tctggagttt gtcaccagtg gaggccggat ggacccaccc aagaactgcc ctgggcctgt   4980

ataccggata atgactcagt gctggcaaca tcagcctgaa gacaggccca actttgccat   5040

cattttggag aggattgaat actgcaccca ggacccggat gtaatcaaca ccgctttgcc   5100

gatagaatat ggtccacttg tggaagagga agagaaagtg cctgtgaggc ccaaggaccc   5160

tgaggggggtt cctcctctcc tggtctctca acaggcaaaa cgggaggagg agcgcagccc   5220

agctgcccca ccacctctgc ctaccacctc ctctggcaag gctgcaaaga aacccacagc   5280

tgcagagatc tctgttcgag tccctagagg gccggccgtg gaagggggac acgtgaatat   5340

ggcattctct cagtccaacc ctccttcgga gttgcacaag gtccacggat ccagaaacaa   5400

gcccaccagc ttgtggaacc caacgtacgg ctcctggttt acagagaaac ccaccaaaaa   5460

gaataatcct atagcaaaga aggagccaca cgacaggggt aacctggggc tggagggaag   5520

ctgtactgtc ccacctaacg ttgcaactgg gagacttccg gggggcctcac tgctcctaga   5580

gccctcttcg ctgactgcca atatgaagga ggtacctctg ttcaggctac gtcacttccc   5640

ttgtgggaat gtcaattacg gctaccagca acagggcttg cccttagaag ccgctactgc   5700

ccctggagct ggtcattacg aggataccat tctgaaaagc aagaatagca tgaaccagcc   5760

tgggccctga gctcggtcgc acactcactt ctcttccttg ggatccctaa gaccgtggag   5820

gagagagagg caatggctcc ttcacaaacc agagaccaaa tgtcacgttt tgttttgtgc   5880

caacctattt tgaagtacca ccaaaaaagc tgtattttga aaatgcttta gaaaggtttt   5940

gagcatgggt tcatcctatt ctttcgaaag aagaaaatat cataaaaatg agtgataaat   6000

acaaggccca gatgtggttg cataaggttt ttatgcatgt ttgttgtata cttccttatg   6060

cttctttcaa attgtgtgtg ctctgcttca atgtagtcag aattagctgc ttctatgttt   6120

catagttggg gtcatagatg tttccttgcc ttgttgatgt ggacatgagc catttgaggg   6180

gagagggaac ggaaataaag gagttatttg taatgactaa aa                      6222
```

<210> SEQ ID NO 7
<211> LENGTH: 1620
<212> TYPE: PRT
<213> ORGANISM: Homo sapiens
<220> FEATURE:
<221> NAME/KEY: MISC_FEATURE -continued
<222> LOCATION: (1)..(1620)
<223> OTHER INFORMATION: Amino acid sequence for human ALK

<400> SEQUENCE: 7

Met Gly Ala Ile Gly Leu Leu Trp Leu Leu Pro Leu Leu Leu Ser Thr
1               5                   10                  15

Ala Ala Val Gly Ser Gly Met Gly Thr Gly Gln Arg Ala Gly Ser Pro
            20                  25                  30

Ala Ala Gly Pro Pro Leu Gln Pro Arg Glu Pro Leu Ser Tyr Ser Arg
        35                  40                  45

Leu Gln Arg Lys Ser Leu Ala Val Asp Phe Val Val Pro Ser Leu Phe
    50                  55                  60

Arg Val Tyr Ala Arg Asp Leu Leu Leu Pro Pro Ser Ser Ser Glu Leu
65                  70                  75                  80

Lys Ala Gly Arg Pro Glu Ala Arg Gly Ser Leu Ala Leu Asp Cys Ala
                85                  90                  95

Pro Leu Leu Arg Leu Leu Gly Pro Ala Pro Gly Val Ser Trp Thr Ala
            100                 105                 110

Gly Ser Pro Ala Pro Ala Glu Ala Arg Thr Leu Ser Arg Val Leu Lys
        115                 120                 125

Gly Gly Ser Val Arg Lys Leu Arg Arg Ala Lys Gln Leu Val Leu Glu
    130                 135                 140

Leu Gly Glu Glu Ala Ile Leu Glu Gly Cys Val Gly Pro Pro Gly Glu
145                 150                 155                 160

Ala Ala Val Gly Leu Leu Gln Phe Asn Leu Ser Glu Leu Phe Ser Trp
                165                 170                 175

Trp Ile Arg Gln Gly Glu Gly Arg Leu Arg Ile Arg Leu Met Pro Glu
            180                 185                 190

Lys Lys Ala Ser Glu Val Gly Arg Glu Gly Arg Leu Ser Ala Ala Ile
        195                 200                 205

Arg Ala Ser Gln Pro Arg Leu Leu Phe Gln Ile Phe Gly Thr Gly His
    210                 215                 220

Ser Ser Leu Glu Ser Pro Thr Asn Met Pro Ser Pro Ser Pro Asp Tyr
225                 230                 235                 240

Phe Thr Trp Asn Leu Thr Trp Ile Met Lys Asp Ser Phe Pro Phe Leu
                245                 250                 255

Ser His Arg Ser Arg Tyr Gly Leu Glu Cys Ser Phe Asp Phe Pro Cys
            260                 265                 270

Glu Leu Glu Tyr Ser Pro Pro Leu His Asp Leu Arg Asn Gln Ser Trp
        275                 280                 285

Ser Trp Arg Arg Ile Pro Ser Glu Glu Ala Ser Gln Met Asp Leu Leu
    290                 295                 300

Asp Gly Pro Gly Ala Glu Arg Ser Lys Glu Met Pro Arg Gly Ser Phe
305                 310                 315                 320

Leu Leu Leu Asn Thr Ser Ala Asp Ser Lys His Thr Ile Leu Ser Pro
                325                 330                 335

Trp Met Arg Ser Ser Ser Glu His Cys Thr Leu Ala Val Ser Val His
            340                 345                 350

Arg His Leu Gln Pro Ser Gly Arg Tyr Ile Ala Gln Leu Leu Pro His
        355                 360                 365

Asn Glu Ala Ala Arg Glu Ile Leu Leu Met Pro Thr Pro Gly Lys His
    370                 375                 380

Gly Trp Thr Val Leu Gln Gly Arg Ile Gly Arg Pro Asp Asn Pro Phe
385                 390                 395                 400

```
Arg Val Ala Leu Glu Tyr Ile Ser Ser Gly Asn Arg Ser Leu Ser Ala
                405                 410                 415

Val Asp Phe Phe Ala Leu Lys Asn Cys Ser Glu Gly Thr Ser Pro Gly
            420                 425                 430

Ser Lys Met Ala Leu Gln Ser Ser Phe Thr Cys Trp Asn Gly Thr Val
        435                 440                 445

Leu Gln Leu Gly Gln Ala Cys Asp Phe His Gln Asp Cys Ala Gln Gly
    450                 455                 460

Glu Asp Glu Ser Gln Met Cys Arg Lys Leu Pro Val Gly Phe Tyr Cys
465                 470                 475                 480

Asn Phe Glu Asp Gly Phe Cys Gly Trp Thr Gln Gly Thr Leu Ser Pro
                485                 490                 495

His Thr Pro Gln Trp Gln Val Arg Thr Leu Lys Asp Ala Arg Phe Gln
            500                 505                 510

Asp His Gln Asp His Ala Leu Leu Leu Ser Thr Thr Asp Val Pro Ala
        515                 520                 525

Ser Glu Ser Ala Thr Val Thr Ser Ala Thr Phe Pro Ala Pro Ile Lys
    530                 535                 540

Ser Ser Pro Cys Glu Leu Arg Met Ser Trp Leu Ile Arg Gly Val Leu
545                 550                 555                 560

Arg Gly Asn Val Ser Leu Val Leu Val Glu Asn Lys Thr Gly Lys Glu
                565                 570                 575

Gln Gly Arg Met Val Trp His Val Ala Ala Tyr Glu Gly Leu Ser Leu
            580                 585                 590

Trp Gln Trp Met Val Leu Pro Leu Leu Asp Val Ser Asp Arg Phe Trp
        595                 600                 605

Leu Gln Met Val Ala Trp Trp Gly Gln Gly Ser Arg Ala Ile Val Ala
    610                 615                 620

Phe Asp Asn Ile Ser Ile Ser Leu Asp Cys Tyr Leu Thr Ile Ser Gly
625                 630                 635                 640

Glu Asp Lys Ile Leu Gln Asn Thr Ala Pro Lys Ser Arg Asn Leu Phe
                645                 650                 655

Glu Arg Asn Pro Asn Lys Glu Leu Lys Pro Gly Glu Asn Ser Pro Arg
            660                 665                 670

Gln Thr Pro Ile Phe Asp Pro Thr Val His Trp Leu Phe Thr Thr Cys
        675                 680                 685

Gly Ala Ser Gly Pro His Gly Pro Thr Gln Ala Gln Cys Asn Asn Ala
    690                 695                 700

Tyr Gln Asn Ser Asn Leu Ser Val Glu Val Gly Ser Glu Gly Pro Leu
705                 710                 715                 720

Lys Gly Ile Gln Ile Trp Lys Val Pro Ala Thr Asp Thr Tyr Ser Ile
                725                 730                 735

Ser Gly Tyr Gly Ala Ala Gly Gly Lys Gly Gly Lys Asn Thr Met Met
            740                 745                 750

Arg Ser His Gly Val Ser Val Leu Gly Ile Phe Asn Leu Glu Lys Asp
        755                 760                 765

Asp Met Leu Tyr Ile Leu Val Gly Gln Gln Gly Glu Asp Ala Cys Pro
    770                 775                 780

Ser Thr Asn Gln Leu Ile Gln Lys Val Cys Ile Gly Glu Asn Asn Val
785                 790                 795                 800

Ile Glu Glu Glu Ile Arg Val Asn Arg Ser Val His Glu Trp Ala Gly
                805                 810                 815
```

-continued

```
Gly Gly Gly Gly Gly Gly Gly Ala Thr Tyr Val Phe Lys Met Lys Asp
            820                 825                 830

Gly Val Pro Val Pro Leu Ile Ile Ala Ala Gly Gly Gly Gly Arg Ala
        835                 840                 845

Tyr Gly Ala Lys Thr Asp Thr Phe His Pro Glu Arg Leu Glu Asn Asn
    850                 855                 860

Ser Ser Val Leu Gly Leu Asn Gly Asn Ser Gly Ala Ala Gly Gly Gly
865                 870                 875                 880

Gly Gly Trp Asn Asp Asn Thr Ser Leu Leu Trp Ala Gly Lys Ser Leu
                885                 890                 895

Gln Glu Gly Ala Thr Gly Gly His Ser Cys Pro Gln Ala Met Lys Lys
            900                 905                 910

Trp Gly Trp Glu Thr Arg Gly Gly Phe Gly Gly Gly Gly Gly Gly Cys
        915                 920                 925

Ser Ser Gly Gly Gly Gly Gly Gly Tyr Ile Gly Gly Asn Ala Ala Ser
    930                 935                 940

Asn Asn Asp Pro Glu Met Asp Gly Glu Asp Gly Val Ser Phe Ile Ser
945                 950                 955                 960

Pro Leu Gly Ile Leu Tyr Thr Pro Ala Leu Lys Val Met Glu Gly His
                965                 970                 975

Gly Glu Val Asn Ile Lys His Tyr Leu Asn Cys Ser His Cys Glu Val
            980                 985                 990

Asp Glu Cys His Met Asp Pro Glu  Ser His Lys Val Ile  Cys Phe Cys
        995                 1000                 1005

Asp His  Gly Thr Val Leu Ala  Glu Asp Gly Val Ser  Cys Ile Val
    1010                 1015                 1020

Ser Pro  Thr Pro Glu Pro His  Leu Pro Leu Ser Leu  Ile Leu Ser
    1025                 1030                 1035

Val Val  Thr Ser Ala Leu Val  Ala Ala Leu Val Leu  Ala Phe Ser
    1040                 1045                 1050

Gly Ile  Met Ile Val Tyr Arg  Arg Lys His Gln Glu  Leu Gln Ala
    1055                 1060                 1065

Met Gln  Met Glu Leu Gln Ser  Pro Glu Tyr Lys Leu  Ser Lys Leu
    1070                 1075                 1080

Arg Thr  Ser Thr Ile Met Thr  Asp Tyr Asn Pro Asn  Tyr Cys Phe
    1085                 1090                 1095

Ala Gly  Lys Thr Ser Ser Ile  Ser Asp Leu Lys Glu  Val Pro Arg
    1100                 1105                 1110

Lys Asn  Ile Thr Leu Ile Arg  Gly Leu Gly His Gly  Ala Phe Gly
    1115                 1120                 1125

Glu Val  Tyr Glu Gly Gln Val  Ser Gly Met Pro Asn  Asp Pro Ser
    1130                 1135                 1140

Pro Leu  Gln Val Ala Val Lys  Thr Leu Pro Glu Val  Cys Ser Glu
    1145                 1150                 1155

Gln Asp  Glu Leu Asp Phe Leu  Met Glu Ala Leu Ile  Ile Ser Lys
    1160                 1165                 1170

Phe Asn  His Gln Asn Ile Val  Arg Cys Ile Gly Val  Ser Leu Gln
    1175                 1180                 1185

Ser Leu  Pro Arg Phe Ile Leu  Leu Glu Leu Met Ala  Gly Gly Asp
    1190                 1195                 1200

Leu Lys  Ser Phe Leu Arg Glu  Thr Arg Pro Arg Pro  Ser Gln Pro
    1205                 1210                 1215

Ser Ser  Leu Ala Met Leu Asp  Leu Leu His Val Ala  Arg Asp Ile
```

-continued

```
    1220                1225                1230

Ala Cys  Gly Cys Gln Tyr Leu  Glu Glu Asn His Phe  Ile His Arg
    1235                1240                1245

Asp Ile  Ala Ala Arg Asn Cys  Leu Leu Thr Cys Pro  Gly Pro Gly
    1250                1255                1260

Arg Val  Ala Lys Ile Gly Asp  Phe Gly Met Ala Arg  Asp Ile Tyr
    1265                1270                1275

Arg Ala  Ser Tyr Tyr Arg Lys  Gly Gly Cys Ala Met  Leu Pro Val
    1280                1285                1290

Lys Trp  Met Pro Pro Glu Ala  Phe Met Glu Gly Ile  Phe Thr Ser
    1295                1300                1305

Lys Thr  Asp Thr Trp Ser Phe  Gly Val Leu Leu Trp  Glu Ile Phe
    1310                1315                1320

Ser Leu  Gly Tyr Met Pro Tyr  Pro Ser Lys Ser Asn  Gln Glu Val
    1325                1330                1335

Leu Glu  Phe Val Thr Ser Gly  Gly Arg Met Asp Pro  Pro Lys Asn
    1340                1345                1350

Cys Pro  Gly Pro Val Tyr Arg  Ile Met Thr Gln Cys  Trp Gln His
    1355                1360                1365

Gln Pro  Glu Asp Arg Pro Asn  Phe Ala Ile Ile Leu  Glu Arg Ile
    1370                1375                1380

Glu Tyr  Cys Thr Gln Asp Pro  Asp Val Ile Asn Thr  Ala Leu Pro
    1385                1390                1395

Ile Glu  Tyr Gly Pro Leu Val  Glu Glu Glu Glu Lys  Val Pro Val
    1400                1405                1410

Arg Pro  Lys Asp Pro Glu Gly  Val Pro Pro Leu Leu  Val Ser Gln
    1415                1420                1425

Gln Ala  Lys Arg Glu Glu Glu  Arg Ser Pro Ala Ala  Pro Pro Pro
    1430                1435                1440

Leu Pro  Thr Thr Ser Ser Gly  Lys Ala Ala Lys Lys  Pro Thr Ala
    1445                1450                1455

Ala Glu  Ile Ser Val Arg Val  Pro Arg Gly Pro Ala  Val Glu Gly
    1460                1465                1470

Gly His  Val Asn Met Ala Phe  Ser Gln Ser Asn Pro  Pro Ser Glu
    1475                1480                1485

Leu His  Lys Val His Gly Ser  Arg Asn Lys Pro Thr  Ser Leu Trp
    1490                1495                1500

Asn Pro  Thr Tyr Gly Ser Trp  Phe Thr Glu Lys Pro  Thr Lys Lys
    1505                1510                1515

Asn Asn  Pro Ile Ala Lys Lys  Glu Pro His Asp Arg  Gly Asn Leu
    1520                1525                1530

Gly Leu  Glu Gly Ser Cys Thr  Val Pro Pro Asn Val  Ala Thr Gly
    1535                1540                1545

Arg Leu  Pro Gly Ala Ser Leu  Leu Leu Glu Pro Ser  Ser Leu Thr
    1550                1555                1560

Ala Asn  Met Lys Glu Val Pro  Leu Phe Arg Leu Arg  His Phe Pro
    1565                1570                1575

Cys Gly  Asn Val Asn Tyr Gly  Tyr Gln Gln Gln Gly  Leu Pro Leu
    1580                1585                1590

Glu Ala  Ala Thr Ala Pro Gly  Ala Gly His Tyr Glu  Asp Thr Ile
    1595                1600                1605

Leu Lys  Ser Lys Asn Ser Met  Asn Gln Pro Gly Pro
    1610                1615                1620
```

-continued

```
<210> SEQ ID NO 8
<211> LENGTH: 20
<212> TYPE: DNA
<213> ORGANISM: Artificial sequence
<220> FEATURE:
<223> OTHER INFORMATION: Forward primer for exon 23 of the ALK gene

<400> SEQUENCE: 8

aagatttgcc cagactcagc                                              20


<210> SEQ ID NO 9
<211> LENGTH: 20
<212> TYPE: DNA
<213> ORGANISM: Artificial sequence
<220> FEATURE:
<223> OTHER INFORMATION: Reverse primer for exon 23 of the ALK gene

<400> SEQUENCE: 9

tgtccttggc acaacaactg                                              20
```

ANAPLASTIC THYROID CANCERS HARBOR NOVEL ONCOGENIC MUTATIONS OF THE ALK GENE

STATEMENT OF GOVERNMENTAL INTEREST

This invention was made with government support under grant number CA113507 awarded by the National Institutes of Health. The government has certain rights in the invention.

CROSS-REFERENCE TO RELATED APPLICATIONS

This application is a 35 U.S.C. §371 U.S. national entry of International Application PCT/US2012/038285 having an international filing date of May 17, 2012, which claims the benefit of U.S. Provisional Application No. 61/487,151, filed May 17, 2011, the content of each of the aforementioned applications is herein incorporated by reference in their entirety.

FIELD OF THE INVENTION

The present invention relates to diagnostic, therapeutic and prognostic methods for thyroid cancers.

INCORPORATION-BY-REFERENCE OF MATERIAL SUBMITTED ELECTRONICALLY

This application contains a sequence listing. It has been submitted electronically via EFS-Web as an ASCII text file entitled “P11563-02_ST25.txt.” The sequence listing is 24,246 bytes in size, and was created on May 15, 2012. It is hereby incorporated by reference in its entirety.

BACKGROUND OF THE INVENTION

Anaplastic lymphoma kinase (ALK) is a member of the insulin receptor subfamily of receptor tyrosine kinases (RTKs), with its encoding gene located on the short arm of chromosome 2 (1, 2), ALK was initially identified as part of an oncogenic fusion gene, NPM1-ALK (also known as NPMALK), in anaplastic large-cell non-Hodgkin’s lymphomas (ALCL; 3). It is also part of the fusion gene EML4-ALK in non-small-cell lung cancer (NSCLC; 4). There are a few other ALK fusion genes, such as TMP3/4-ALK and RANBP2-ALK, in inflammatory myofibroblastic tumors (IMT; 5). The tyrosine kinase activities of these fusion ALK proteins are aberrantly activated and promote cell proliferation and survival (6, 7). ALK fusion proteins have also been shown to activate various signaling pathways, among which are the phosphatidylinositol 3-kinase (PI3K)/Akt pathway and the Ras→Raf→MEK→extracellular signal regulated kinase (ERK)/mitogen-activated protein (MAP) kinase pathway with multiple interaction points to mediate the ALK signaling (8, 9).

Recently, ALK mutations were found in 6% to 14% of sporadic neuroblastomas (10-14). ALK mutations were also reported in familial neuroblastomas (13, 14). Moreover, genetic amplification of the ALK gene could also occur in neuroblastomas or cell lines derived from this tumor (10, 11, 13, 15). Except for occasional mutations in the juxtamembrane domain, most ALK mutations identified so far are within the tyrosine kinase domain of ALK. ALK mutations and/or copy gain were found particularly in advanced and metastatic neuroblastomas, and patients with ALK mutations had a worse prognosis (11, 12, 14). Several common ALK mutations were shown to be functional. For example, siRNA-mediated knockdown of the ALK expression in cell lines harboring ALK mutants F1174L or R1275Q caused cell apoptosis and suppression of cell proliferation (12-14). The F1174L and another mutant ALK, K1062M, were shown to display increased tyrosine kinase activity and promote cell focus formation, cell transformation, and xenograft tumorigenecity in nude mice (10). The oncogenicity of ALK F1174L and R1275Q was also shown in another study (12). Genetic copy gain of the ALK is also functionally important, as suggested by the demonstration that inhibition of ALK in neuroblastoma cell lines harboring ALK copy gain induced cell apoptosis through reduced signaling of the PI3K/Akt and MAP kinase pathways (15).

Mutations of the ALK gene have not been reported in human cancers other than neuroblastomas. As described herein, the present inventors investigated the mutation status of the ALK gene in various thyroid cancers, including well-differentiated papillary thyroid cancer (PTC) and follicular thyroid cancer (FTC) and undifferentiated anaplastic thyroid cancer (ATC). Prompted by the finding of ALK mutations in ATC, a rapidly aggressive and deadly human cancer (16), the present inventors also examined melanoma and colon carcinoma for ALK mutation. Indeed, identifying mutations in human cancers is highly desirable because it can lead to the development of new therapeutics that target such fusion or mutant proteins, and to new diagnostics for identifying patients that have such gene mutations.

SUMMARY OF THE INVENTION

The present invention is based, at least in part, on the discovery of ALK gene mutations in thyroid cancer that may rationalize clinical evaluation of ALK inhibitors in this setting. In undifferentiated anaplastic thyroid cancer (ATC), the present inventors identified two novel point mutations in exon 23 of the ALK gene, C3592T and G3602A, in exon 23 of the ALK gene with a prevalence of 11.11%, but found no mutations in the matched normal tissues or in well-differentiated thyroid cancers. These two mutations, resulting in the L1198F and G1201E amino acid changes, respectively, both reside within the ALK tyrosine kinase domain where they dramatically increased tyrosine kinase activities. Similarly, these mutations heightened the ability of ALK to activate the PI3K/Akt and MAP kinase pathways in established mouse cells. Further investigation demonstrated that these two ALK mutants strongly promoted cell focus formation, anchorage-independent growth, and cell invasion. Similar oncogenic properties were observed in the neuroblastoma-associated ALK mutants K1062M and F1174L, but not in wild-type ALK. Overall, the results reveal two novel gain-of-function mutations of ALK in certain ATCs and they suggest efforts to clinically evaluate the use of ALK kinase inhibitors to treat patients who harbor ATCs with these mutations.

Furthermore, although these two novel mutations are found in thyroid cancer, they likely are also present in other human cancers and can therefore make ALK an effective therapeutic target also in those non-thyroid cancers harboring them. Indeed, the molecular testing of these two novel ALK mutations in thyroid cancer as well as in other human cancers will be helpful in guiding their targeted treatments. These cancers may particularly include brain tumor, lymphoma, lung cancer, gastric cancer, pancreatic cancer, liver cancer, colon cancer, melanoma, breast cancer, ovarian cancer, cervical cancer, prostate cancer, testicle cancer, bone cancer, head and neck cancer, laryngeal cancer, leukemia, myofibroblastic tumors, and other cancers.

Accordingly, in one aspect, the present invention provides methods for treating thyroid cancer. In one embodiment, a method for treating an anaplastic thyroid cancer (ATC) patient comprises the step of administering to the patient an effective amount of an anaplastic lymphoma kinase (ALK) inhibitor. In a specific embodiment, the ALK inhibitor is crizotinib. In another embodiment, the patient has a C3592T mutation in exon 23 of the ALK gene. In yet another embodiment, the patient has a G3602A mutation in exon 23 of the ALK gene. The can further comprise the step of determining whether the patient has a C3592T and/or a G3602A mutation in exon 23 of the ALK gene prior to the administering step.

In another embodiment, a method for treating anaplastic thyroid cancer (ATC) in a thyroid cancer patient comprises the steps of (a) determining whether the thyroid cancer patient has a C3592T and/or a G3602A mutation in exon 23 of the anaplastic lymphoma kinase (ALK) gene; and (b) treating the patient with an ALK inhibitor therapy if the patient has either or both of the mutations. Alternatively, a method for treating anaplastic thyroid cancer (ATC) in a thyroid cancer patient comprises the step of treating the patient with an ALK inhibitor therapy if the thyroid cancer patient has a C3592T and/or a G3602A mutation in exon 23 of the ALK gene. In such embodiments, the ALK inhibitor is crizotinib.

In another aspect, the present invention provides methods for treating cancer patients that harbor the mutations described herein. For example, a method for treating a cancer patient comprises the step of administering to the patient an effective amount of an ALK inhibitor, wherein the cancer patient has a C3592T and/or a G3602A mutation in exon 23 of the ALK gene. In another embodiment, a method for treating a cancer patient comprises the steps of (a) determining whether the cancer patient has a C3592T mutation in exon 23 of the anaplastic lymphoma kinase (ALK) gene; and (b) treating the patient with an ALK inhibitor therapy if the patient has either or both of the mutations. In such embodiments, the ALK inhibitor is crizotinib. In other specific embodiments, the cancer is a neuroblastoma.

In another specific embodiment, a method for treating a neuroblastoma cancer patient comprises the step of administering to the patient an effective amount of an ALK inhibitor, wherein the patient has a C3592T and/or a G3602A mutation in exon 23 of the ALK gene. In a more specific embodiment, the ALK inhibitor is crizotinib.

In additional embodiments, the methods described herein can further comprise the step of administering an inhibitor of the PI3K/Akt pathway. In other embodiments, the methods described herein can further comprise the step of administering an inhibitor of the MAP kinase pathway. In a specific embodiment, a method for treating a cancer patient comprises the step of administering to the patient an inhibitor of a protein or pathway selected from the group consisting of ALK, the PI3K/Akt pathway and the MAP kinase pathway, wherein the patient has a C3592T and/or a G3602A mutation in exon 23 of the ALK gene. In a more specific embodiment, the ALK inhibitor is crizotinib. In another embodiment, the patient has ATC. In yet another embodiment, the patient has a neuroblastoma.

In another aspect, the present invention provides diagnostic and prognostic methods relating to the mutations described herein. In one embodiment, a method for diagnosing ATC in patient comprises the step of performing an assay on a biological sample from the patient to identify the presence or absence of a C3592T and/or a G3602A mutation in exon 23 of the ALK gene according to SEQ ID NO:6, wherein the presence of either of both of the mutations correlates with a diagnosis of ATC in the patient. In another embodiment, a method for determining a patient's risk of developing ATC comprises the step of performing an assay on a biological sample from the patient to identify the presence or absence of a C3592T and/or a G3602A mutation in exon 23 of the ALK gene according to SEQ NO:6, wherein the presence of either of both of the mutations correlates with a prognosis that the patient has a higher risk of ATC than a patient without the mutations, and wherein the absence of the mutations correlates with a prognosis that the patient has a lower risk of ATC than a patient with either or both of the mutations.

In a more specific embodiment, a method for detecting ATC in a patient comprises the step of determining the presence of a C3592T and/or a G3602A mutation in exon 23 of the ALK gene according to SEQ ID NO:6 in a blood sample of a patient, wherein the presence of the mutation indicates ATC in the patient.

In yet another embodiment, a method for distinguishing ATC from non-ATC samples comprises the step of determining the presence of a C3592T and/or a G3602A mutation in exon 23 of the ALK gene according to SEQ ID NO:6 in thyroid sample of a patient, wherein the presence of either or both of the mutations indicates ATC and absence of either or both of the mutations indicates non-ATC. In a specific embodiment, the thyroid sample is a fine needle aspirate (FNA). In another embodiment, the thyroid sample is a tissue sample. In yet another embodiment, the thyroid sample is a cytological sample. The mutations can be detected using methods and kits known to those of ordinary skill in the art. For example, as described below, genomic DNA can be isolated from a sample and then exon 23 can be PCR amplified and sequenced. The method may further comprise providing a diagnosis based on the presence or absence of either or both of the mutations.

BRIEF DESCRIPTION OF THE FIGURES

FIG. 2 shows the increased tyrosine kinase activities of ALK mutants L1198F and G1201E and their activation of the PI3K/Akt and MAP kinase pathways.

FIG. 3 shows the focus-formation and anchorage-independent growth of cells promoted by ALK mutants. FIG. 3C shows the anchorage-independent cell growth of ALK mutants on soft agar. NIH3T3 cells stably transfected with Flag-tagged vector, wild-type ALK, and each of the ALK mutants indicated were seeded in soft agar, and colonies formed 4 weeks later were photographed with 40× magnification. FIG. 3D shows the analyses of the number of colonies. The number of cell colonies corresponding to C that were greater than 0.1 mm in diameter was counted. Results represent mean±SD of 3 independent experiments.

FIG. 4 shows cell invasion promoted by ALK mutants.

DETAILED DESCRIPTION OF THE INVENTION

Figure 1A:
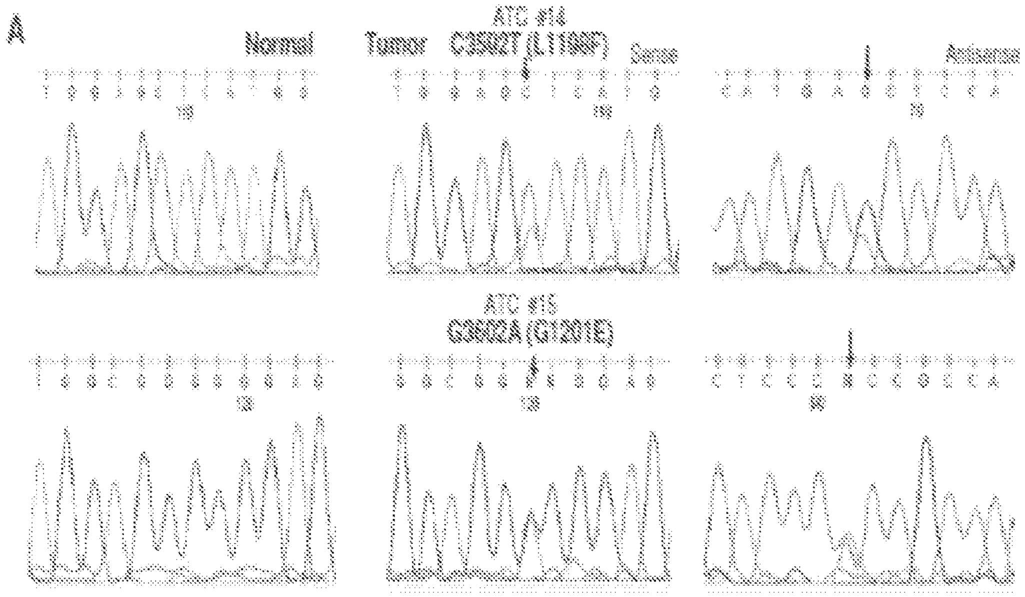
FIG. 1A is a sequencing electropherogram of the ALK gene. Left, the sequencing results of the matched normal tissues of the 2 ATC cases, showing the wild-type ALK gene. Middle and right, the sequencing results of 2 ATC tumors. Top, the sequencing results of sense and antisense strands of a region of exon 23 of the ALK gene in an ATC showing the heterozygous C>T mutation at nucleotide position 3,592 in codon 1,198, resulting in the L1198F amino acid change of ALK. Bottom, the sequencing results of sense and antisense strands of a region of exon 23 of the ALK gene in another ATC showing the heterozygous G>A mutation at nucleotide position 3,602 in codon 1,201, resulting in the G1201E amino acid change. Arrows indicate the mutated nucleotides. Nucleotide numbers refer to the position within the coding sequence of the ALK gene, where position 1 corresponds to the first position of the translation initiation codon. All samples were sequenced in 2 repeated experiments with independent PCR by sense and antisense primers.

It is understood that the present invention is not limited to the particular methods and components, etc., described herein, as these may vary. It is also to be understood that the terminology used herein is used for the purpose of describing particular embodiments only, and is not intended to limit the scope of the present invention. It must be noted that as used herein and in the appended claims, the singular forms "a," "an," and "the" include the plural reference unless the context clearly dictates otherwise. Thus, for example, a reference to a "protein" is a reference to one or more proteins, and includes equivalents thereof known to those skilled in the art and so forth.

Unless defined otherwise, all technical and scientific terms used herein have the same meaning as commonly understood by one of ordinary skill in the art to which this invention belongs. Specific methods, devices, and materials are described, although any methods and materials similar or equivalent to those described herein can be used in the practice or testing of the present invention.

All publications cited herein are hereby incorporated by reference including all journal articles, books, manuals, published patent applications, and issued patents. In addition, the meaning of certain terms and phrases employed in the specification, examples, and appended claims are provided. The definitions are not meant to be limiting in nature and serve to provide a clearer understanding of certain aspects of the present invention.

I. Definitions

The term "ALK inhibitor" refers to an agent that inhibits the synthesis or biological activity of ALK. ALK inhibitors are known in the art and are described herein. The term also includes agents that have activity in addition to ALK inhibitory activity.

As used herein, the term "effective," means adequate to accomplish a desired, expected, or intended result. More particularly, a "therapeutically effective amount" as provided herein refers to an amount of an ALK inhibitor of the present invention, either alone or in combination with another therapeutic agent, necessary to provide the desired therapeutic effect, e.g., an amount that is effective to prevent, alleviate, or ameliorate symptoms of disease or prolong the survival of the subject being treated. In a specific embodiment, the term "therapeutically effective amount" as provided herein refers to an amount of an ALK inhibitor, necessary to provide the desired therapeutic effect, e.g., an amount that is effective to prevent, alleviate, or ameliorate symptoms of disease or prolong the survival of the subject being treated. As would be appreciated by one of ordinary skill in the art, the exact amount required will vary from subject to subject, depending on age, general condition of the subject, the severity of the condition being treated, the particular compound and/or composition administered, and the like. An appropriate "therapeutically effective amount" in any individual case can be determined by one of ordinary skill in the art by reference to the pertinent texts and literature and/or by using routine experimentation.

As used herein, the terms "treatment," "treating," and the like, refer to obtaining a desired pharmacologic and/or physiologic effect. The effect may be prophylactic in terms of completely or partially preventing a disease or symptom thereof and/or may be therapeutic in terms of a partial or complete cure for a disease and/or adverse affect attributable to the disease. "Treatment," as used herein, covers any treatment of a disease in a subject, particularly in a human, and includes: (a) preventing the disease from occurring in a subject which may be predisposed to the disease but has not yet been diagnosed as having it; (b) inhibiting the disease, i.e., arresting its development; and (c) relieving the disease, e.g., causing regression of the disease, e.g., to completely or partially remove symptoms of the disease.

As used herein, the term "antibody" is used in reference to any immunoglobulin molecule that reacts with a specific antigen. It is intended that the term encompass any immunoglobulin (e.g., IgG, IgM, IgA, IgE, IgD, etc.) obtained from any source (e.g., humans, rodents, non-human primates, caprines, bovines, equines, ovines, etc.). Specific types/examples of antibodies include polyclonal, monoclonal, humanized, chimeric, human, or otherwise-human-suitable antibodies. "Antibodies" also includes any fragment or derivative of any of the herein described antibodies. In specific embodiments, antibodies may be raised against ALK and used as ALK inhibitors.

The terms "specifically binds to," "specific for," and related grammatical variants refer to that binding which occurs between such paired species as antibody/antigen, enzyme/substrate, receptor/agonist, and lectin carbohydrate which may be mediated by covalent or non-covalent interactions or a combination of covalent and non-covalent interactions. When the interaction of the two species produces a non-covalently bound complex, the binding which occurs is typically electrostatic, hydrogen-bonding, or the result of lipophilic interactions. Accordingly, "specific binding" occurs between a paired species where there is interaction between the two which produces a bound complex having the characteristics of an antibody/antigen or enzyme/substrate interaction. In particular, the specific binding is characterized by the binding of one member of a pair to a particular species and to no other species within the family of compounds to which the corresponding member of the binding member belongs. Thus, for example, an antibody typically binds to a single epitope and to no other epitope within the family of proteins. In some embodiments, specific binding between an antigen and an antibody will have a binding affinity of at least $10^{-6}$ M. In other embodiments, the antigen and antibody will bind with affinities of at least $10^{-7}$ M, $10^{-8}$ M to $10^{-9}$ M, $10^{-10}$ M, $10^{-11}$ M, or $10^{-12}$ M.

Optional" or "optionally" means that the subsequently described event or circumstance can or cannot occur, and that the description includes instances where the event or circumstance occurs and instances where it does not.

As used herein, a "subject" or "patient" means an individual and can include domesticated animals, (e.g., cats, dogs, etc.); livestock (e.g., cattle, horses, pigs, sheep, goats, etc.), laboratory animals (e.g., mouse, rabbit, rat, guinea pig, etc.) and birds. In one aspect, the subject is a mammal such as a primate or a human. In particular, the term also includes mammals diagnosed with cancer.

The terms "sample," "patient sample," "biological sample," and the like, encompass a variety of sample types obtained from a patient, individual, or subject and can be used in a diagnostic or monitoring assay. The patient sample may be obtained from a healthy subject, a diseased patient or a patient having associated symptoms of cancer (e.g., anaplastic thyroid cancer). Moreover, a sample obtained from a patient can be divided and only a portion may be used for diagnosis. Further, the sample, or a portion thereof, can be stored under conditions to maintain sample for later analysis. The definition specifically encompasses blood and other liquid samples of biological origin (including, but not limited to, peripheral blood, serum, plasma, cerebrospinal fluid, urine, saliva, stool and synovial fluid), solid tissue samples such as a biopsy specimen or tissue cultures or cells derived therefrom and the progeny thereof. In a specific embodiment, a sample comprises a blood sample. In another embodiment, a sample comprises a plasma sample. In yet another embodiment, a serum sample is used.

The definition of "sample" also includes samples that have been manipulated in any way after their procurement, such as by centrifugation, filtration, precipitation, dialysis, chromatography, treatment with reagents, washed, or enriched for certain cell populations. The terms further encompass a clinical sample, and also include cells in culture, cell supernatants, tissue samples, organs, and the like. Samples may also comprise fresh-frozen and/or formalin-fixed, paraffin-embedded tissue blocks, such as blocks prepared from clinical or pathological biopsies, prepared for pathological analysis or study by immunohistochemistry.

The term "inhibitor" includes any type of molecule or agent that directly or indirectly inhibits the expression or activity of a target gene or protein. An inhibitor can be any type of compound, such as a small molecule, antibody or antisense compound. In certain embodiments, the target gene or protein is ALK. In other embodiments, the target gene or protein is a member of the PI3K/Akt pathway. The PI3K/Akt pathway is a signaling pathway involved in a number of cellular processes, such as cell growth, proliferation, differentiation, motility, survival, intracellular trafficking, metabolism and angiogenesis. In the context of the present disclosure, members of the PI3K/Akt pathway include, but are not limited to, PIK3CA, PIK3D, PIK3B, Ras, and PTEN. Inhibitors of the PI3K/Akt pathway include, for example, Akt inhibitors, such as perifosine and triciribine; mTOR inhibitors, such as temsirolimus, everolimus; receptor tyrosine kinase inhibitors, e.g., motesanib, axitinib, sunitinib; and inhibitors of other signaling pathways, such as the NF-kappa pathway.

In some embodiments, the target gene or protein is a member of the MAP kinase pathway. Members of the MAP kinase pathway include, for example, Grb-2, mSOS, Rsk1, BRAF, RET/PTC, Ras, MEK, and ERK Inhibitors of the MAP kinase pathways include, for example, MEK inhibitors, such as CI-1040, PD0325901, AZD6244, RDEA119, RDEA436; Raf inhibitors, such as PLX4720, BAY 43-9006 (sorafenib). When the two pathways are to be inhibited, two distinct inhibitors of two distinct proteins can be used. Multiple inhibitors of each pathway may also be used, if desired. Certain inhibitors such as Ras inhibitors may act on both pathways and these may also be used in the invention.

II. Anaplastic Lymphoma Kinase Inhibitors

In particular embodiments, the present invention utilizes ALK inhibitors. ALK inhibitors are known in the art and include PF-2341066 or Crizotnib and related analogs. See WO2006021886 and WO2004076412 (Pfizer), WO2007130168 (Cephalon), WO2009154769 (Xcovery), WO201056311 and WO2010068292 (Ariad), and WO201059771 (OSI Pharmaceuticals). In other embodiments, ALK inhibitors may comprise the 2,4-diaminopyrimidine pharmacophore kinase inhibitor motif. See WO2004080980 (e.g., NVP-TAE226 and NVP-TAE 684), WO2005026130, WO2005016894, WO2005026158, WO2006021357, WO2008073687, WO209158431, WO2009032668, and WO 201002655 (Novartis). See also WO2008051547 (Cephalon) and WO2009143389 (Ariad). Other ALK inhibitors are based on bicyclic diaminopyrimidine scaffolds. See WO2009032703, WO2009126514, and WO2009126515 (Novartis); WO2009020990 and WO2010045451 (e.g., GSK1838705A, GSK), WO2009008371 (Astellas), WO2009143389 (Ariad), WO2009132202 (Incyte).

A pyridone-based scaffold is also useful for ALK inhibition. See WO2008021369 and WO2009117097 (Chembridge/St. Jude's Research Hospital), and Bristol-Myers Squib (BMS-536294 and BMS-695735). ALK inhibitors may also comprise triazine pyrazole compounds. See WO2009143389 (AstraZeneca) and WO2009015254 (Bristol-Myers Squib). In other embodiments, pyrazoloisoquinoline inhibitors may be used. See WO2005009389 (Exelixis).

ALK Inhibitors may also include amidothiazoles and amidoimidazoles (WO2005097765 (Exelixis) and WO2009121535 (Universita Degli Studi di Milano, Universite de Geneve, and Universite Claue Bernard Lyon)); α-carboline ALK inhibitors (WO2010025872 (Universita Degli Studi di Milano, Universite de Geneve, and Universite Claue Bernard Lyon); and amidoindazole ALK inhibitors (WO2008074749, WO200913126, WO2009138440 and WO201069966 (Nerviano Medical Sciences)).

III. Antibodies to ALK

The present invention contemplates the use of antibodies specific for ALK in the treatment of cancer including ATC. Such antibodies can inhibit ALK kinase activity or inhibits its ability to bind to fusion proteins. See WO2007124610 and WO2008131575 (Esbatech), WO2007059300 (Medimmune), U.S. Patent Publication No. 20110159008 (Delenex Therapeutics AG).

The phrases "binding specificity," "binding specifically to, "specific binding" or otherwise any reference to an antibody to ALK, refers to a binding reaction that is determinative of the presence of the corresponding ALK antigen to the antibody in a heterogeneous population of antigens and other biologics. The parameters required to achieve such specificity can be determined routinely, using conventional methods in the art including, but not limited to, competitive binding studies. The binding affinity of an antibody can also be readily determined, for example, by Scatchard analysis (Scatchard, Ann. NY Acad. Sci. 51: 660-672, 1949). In some embodiments, the immunoglobulins of the present invention bind to ALK at least about 5, at least about 10, at least about 100, at least about $10^3$, at least about $10^4$, at least $10^5$, and at least $10^6$ fold higher than to other proteins.

Various procedures known in the art may be used for the production of antibodies to ALK or any subunit thereof, or a fragment, derivative, homolog or analog of the protein. Antibodies of the present invention include, but are not limited to, synthetic antibodies, polyclonal antibodies, monoclonal antibodies, recombinantly produced antibodies, intrabodies, multispecific antibodies (including bi-specific antibodies), human antibodies, humanized antibodies, chimeric antibodies, synthetic antibodies, single-chain Fvs (scFv) (including bi-specific scFvs), single chain antibodies Fab fragments, F(ab') fragments, disulfide-linked Fvs (sdFv), and anti-idiotypic (anti-Id) antibodies, and epitope-binding fragments of any of the above. In particular, antibodies of the present invention include immunoglobulin molecules and immunologically active portions of immunoglobulin molecules, e.g., molecules that contain an antigen binding site that immunospecifically binds to an antigen (e.g., one or more complementarity determining regions (CDRs) of an antibody).

Another embodiment for the preparation of antibodies according to the invention is the use of peptide mimetics. Mimetics are peptide-containing molecules that mimic elements of protein secondary structure. See, for example, Johnson et al., "Peptide Turn Mimetics" in BIOTECHNOLOGY AND PHARMACY, Pezzuto et al., Eds., Chapman and Hall, New York (1993). The underlying rationale behind the use of peptide mimetics in rational design is that the peptide backbone of proteins exists chiefly to orient amino acid side chains in such a way as to facilitate molecular interactions, such as those of antibody and antigen. A peptide mimetic is expected to permit molecular interactions similar to the natural molecule. These principles may be used to engineer second generation molecules having many of the natural properties of the targeting antibodies disclosed herein, but with altered and even improved characteristics. More specifically, under this rational design approach, peptide mapping may be used to determine "active" antigen recognition residues, and along with molecular modeling and molecular dynamics trajectory analysis, peptide mimic of the antibodies containing antigen contact residues from multiple CDRs may be prepared.

In some embodiments, an antibody specifically binds an epitope of the ALK protein. It is to be understood that the peptide regions may not necessarily precisely map one epitope, but may also contain an ALK sequence that is not immunogenic. Methods of predicting other potential epitopes to which an immunoglobulin of the invention can bind are well-known to those of skill in the art and include, without limitation, Kyte-Doolittle Analysis (Kyte, J. and Dolittle, R. F., 157 J. Mol. Biol. 105-32 (1982)); Hopp and Woods Analysis (Hopp, T. P. and Woods, K. R., 78 Proc. Natl. Acad. Sci. USA 3824-28 (1981); Hopp, T. J. and Woods, K. R., 20 Mol. Immunol. 483-89 (1983); Hopp, T. J., 88 J. Immunol. Methods 1-18 (1986)); Jameson-Wolf Analysis (Jameson, B. A. and Wolf, H., 4 Comput. Appl. Biosci. 181-86 (1988)); and Emini Analysis (Emini et al., 140 Virology 13-20 (1985)).

Amino acid sequence variants of the antibodies of the present invention may be prepared by introducing appropriate nucleotide changes into the polynucleotide that encodes the antibody or by peptide synthesis. Such modifications include, for example, deletions from, and/or insertions into and/or substitutions of, residues within the amino acid sequences of the antibody. Any combination of deletions, insertions, and substitutions may be made to arrive at the final construct.

Amino acid sequence insertions include amino-terminal and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue or the antibody fused to a cytotoxic polypeptide. Other insertional variants of the antibody molecule include the fusion to the N- or C-terminus of the antibody of a polypeptide that increases the serum half-life of the antibody.

Another type of antibody variant is an amino acid substitution variant. These variants have at least one amino acid residue in the antibody molecule replaced by a different residue. For example, the sites of greatest interest for substitutional mutagenesis of antibodies include the hypervariable regions, but framework region (FR) alterations are also contemplated.

A useful method for the identification of certain residues or regions of the ALK antibodies that are preferred locations for substitution, i.e., mutagenesis, is alanine scanning mutagenesis. See Cunningham & Wells, 244 SCIENCE 1081-85 (1989). Briefly, a residue or group of target residues are identified (e.g., charged residues such as arg, asp, his, lys, and glu) and replaced by a neutral or negatively charged amino acid (most preferably alanine or polyalanine) to affect the interaction of the amino acids with antigen. The amino acid locations demonstrating functional sensitivity to the substitutions are refined by introducing further or other variants at, or for, the sites of substitution. Thus, while the site for introducing an amino acid sequence variation is predetermined, the nature of the mutation per se need not be predetermined. For example, to analyze the performance of a mutation at a given site, alanine scanning or random mutagenesis may be conducted at the target codon or region and the expressed antibody variants screened for the desired activity.

Substantial modifications in the biological properties of the antibody can be accomplished by selecting substitutions that differ significantly in their effect on, maintaining (i) the structure of the polypeptide backbone in the area of the substitution, for example, as a sheet or helical conformation, (ii) the charge or hydrophobicity of the molecule at the target site, or (iii) the bulk of the side chain. Naturally occurring residues are divided into groups based on common side-chain properties:

(1) hydrophobic: norleucine, met, ala, val, leu, ile;
(2) neutral hydrophilic: cys, ser, thr;
(3) acidic: asp, glu;
(4) basic: asn, gln, his, lys, arg;
(5) residues that influence chain orientation: gly, pro; and
(6) aromatic: trp, tyr, phe.

Non-conservative substitutions will entail exchanging a member of one of these classes for another class. Conservative substitutions involve exchanging of amino acids within the same class.

Any cysteine residue not involved in maintaining the proper conformation of the antibody also may be substituted, generally with serine, to improve the oxidative stability of the molecule and prevent aberrant crosslinking. Conversely, cysteine bond(s) may be added to the antibody to improve its stability, particularly where the antibody is an immunoglobulin fragment such as an Fv fragment.

Another type of substitutional variant involves substituting one or more hypervariable region residues of a parent antibody. Generally, the resulting variant(s), i.e., functional equivalents as defined above, selected for further development will have improved biological properties relative to the parent antibody from which they are generated. A convenient way for generating such substitutional variants is by affinity maturation using phage display. Briefly, several hypervariable region sites (e.g., 6-7 sites) are mutated to generate all possible amino substitutions at each site. The antibody variants thus generated are displayed in a monovalent fashion from filamentous phage particles as fusions to the gene III product of M13 packaged within each particle. The phage-displayed variants are then screened for their biological activity (e.g., binding affinity) as herein disclosed.

In order to identify candidate hypervariable region sites for modification, alanine-scanning mutagenesis may be performed to identify hypervariable region residues contributing significantly to antigen binding. Alternatively, or additionally, it may be beneficial to analyze a crystal structure of the antibody-antigen complex to identity contact points between the antibody and antigen. Such contact residues and neighboring residues are candidates for substitution according to the techniques elaborated herein. Once generated, the panel of variants is subjected to screening as described herein and antibodies with superior properties in one or more relevant assays may be selected for further development.

It may be desirable to modify the antibodies of the present invention, i.e., create functional equivalents, with respect to effector function, e.g., so as to enhance antigen-dependent cell-mediated cyotoxicity (ADCC) and/or complement dependent cytotoxicity (CDC) of the antibody. This may be achieved by introducing one or more amino acid substitutions in an Fc region of an antibody. Alternatively or additionally, cysteine residue(s) may be introduced in the Fc region, thereby allowing interchain disulfide bond formation in this region. The homodimeric antibody thus generated may have improved internalization capability and/or increased complement-mediated cell killing and antibody-dependent cellular cytotoxicity (ADCC). Caron et al., 176 J. EXP MED. 1191-95 (1992); Shopes, 148 J. IMMUNOL. 2918-22 (1992). Homodimeric antibodies with enhanced anti-tumor activity may also be prepared using heterobifunctional cross-linkers as described in Wolff et al., 53 CANCER RESEARCH 2560-65 (1993). Alternatively, an antibody can be engineered which has dual Fc regions and may thereby have enhanced complement lysis and ADCC capabilities. Stevenson et al., 3 ANTI-CANCER DRUG DESIGN 219-30 (1989).

To increase the serum half life of an antibody, one may incorporate a salvage receptor binding epitope into the antibody (especially an immunoglobulin fragment) as described in, for example, U.S. Pat. No, 5,739,277. As used herein, the term "salvage receptor binding epitope" refers to an epitope of the Fc region of an IgG molecule (e.g., IgG1, IgG2, IgG3, or IgG4) that is responsible for increasing the in vivo serum half-life of the IgG molecule.

Polynucleotide molecules encoding amino acid sequence variants of the antibody are prepared by a variety of methods known in the art. These methods include, but are not limited to, isolation from a natural source (in the case of naturally occurring amino acid sequence variants) or preparation by oligonucleotide-mediated (or site directed) mutagenesis, PCR mutagenesis, and cassette mutagenesis of an earlier prepared variant or a non-variant version of the anti-ALK antibodies of the present invention.

IV. Other ALK Inhibitors

A. RNA Interference Compositions for Targeting ALK mRNAs

In one aspect of the present invention, the expression of ALK may be inhibited by the use of RNA interference techniques (RNAi). RNAi is a remarkably efficient process whereby double-stranded RNA (dsRNA) induces the sequence-specific degradation of homologous mRNA in animals and plant cells. See Hutvagner and Zamore, 12 CURR. OPIN. GENET. DEV. 225-32 (2002); Hammond et al., 2 NATURE REV. GEN. 110-19 (2001); Sharp, 15 GENES DEV. 485-90 (2001). RNAi can be triggered, for example, by nucleotide (nt) duplexes of small interfering RNA (siRNA) (Chiu et al, 10 MOL. CELL. 549-61 (2002); Elbashir et al., 411 Nature 494-98 (2001)), micro-RNAs (miRNA), functional small-hairpin RNA (shRNA), or other dsRNAs which are expressed in-vivo using DNA templates with RNA polymerase III promoters. See, e.g., Zeng et al., 9 MOL. CELL. 1327-33 (2002); Paddison et al., 16 GENES DEV. 948-58 (2002); Lee et al., 20 NATURE BIOTECHNOL. 500-05 (2002); Paul et al., 20 NATURE BIOTECHNOL. 505-08 (2002); Tuschl, 20 NATURE BIOTECHNOL. 440-48 (2002); Yu et al., 99(9) PROC. NATL. ACAD. SCI. USA, 6047-52 (2002); McManus et al., 8 RNA 842-50 (2002); Sui et al., 99(6) PROC. NATL. ACAD. SCI. USA 5515-20 (2002).

1. Small Interfering RNA

In particular embodiments, the present invention features "small interfering RNA molecules" ("siRNA molecules" or "siRNA"), methods of making siRNA molecules and methods for using siRNA molecules (e.g., research and/or therapeutic methods). The siRNAs of this invention encompass any siRNAs that can modulate the selective degradation of ALK mRNA.

In a specific embodiment, the siRNA of the present invention may comprise double-stranded small interfering RNA molecules (ds-siRNA). A ds-siRNA molecule of the present invention may be a duplex made up of a sense strand and a complementary antisense strand, the antisense strand being sufficiently complementary to a target ALK mRNA to mediate RNAi. The siRNA molecule may comprise about 10 to about 50 or more nucleotides. More specifically, the siRNA molecule may comprise about 16 to about 30, e.g., 16, 17, 18, 19, 20, 21, 22, 23, 24, 25, 26, 27, 28, 29, or 30 nucleotides in each strand. The strands may be aligned such that there are at least 1, 2, or 3 bases at the end of the strands which do not align (e.g., for which no complementary bases occur in the opposing strand) such that an overhang of 1, 2 or 3 residues occurs at one or both ends of the duplex when strands are annealed.

In an alternative embodiment, the siRNA of the present invention may comprise single-stranded small interfering RNA molecules (ss-siRNA); Similar to the ds-siRNA molecules, the ss-siRNA molecule may comprise about 10 to about 50 or more nucleotides. More specifically, the ss-siRNA molecule may comprise about 15 to about 45 or more nucleotides. Alternatively, the ss-siRNA molecule may comprise about 19 to about 40 nucleotides. The ss-siRNA molecules of the present invention comprise a sequence that is "sufficiently complementary" to a target mRNA sequence to direct target-specific RNA interference (RNAi), as defined herein, e.g., the ss-siRNA has a sequence sufficient to trigger the destruction of the target mRNA by the RNAi machinery or process. In one embodiment, the ss-siRNA molecule can be designed such that every residue is complementary to a residue in the target molecule. Alternatively, substitutions can be made within the molecule to increase stability and/or enhance processing activity of the molecule. Substitutions can be made within the strand or can be made to residues at the ends of the strand. In a specific embodiment, the 5'-terminus may be phosphorylated (e.g., comprises a phosphate, diphosphate, or triphosphate group). In another embodiment, the 3' end of an siRNA may be a hydroxyl group in order to facilitate RNAi, as there is no requirement for a 3' hydroxyl group when the active agent is a ss-siRNA molecule. In other instances, the 3' end (e.g., C3 of the 3' sugar) of ss-siRNA molecule may lack a hydroxyl group (e.g., ss-siRNA molecules lacking a 3' hydroxyl or C3 hydroxyl on the 3' sugar (e.g., ribose or deoxyribose).

In another aspect, the siRNA molecules of the present invention may be modified to improve stability under in vitro and/or in vivo conditions, including, for example, in serum and in growth medium for cell cultures. In order to enhance the stability, the 3'-residues may be stabilized against degradation, e.g., they may be selected such that they consist of purine nucleotides, particularly adenosine or guanosine nucleotides. Alternatively, substitution of nucleotides by modified analogues, e.g., substitution of uridine by 2'-deoxythymidine is tolerated and does not affect the efficiency of RNA interference. For example, the absence of a 2' hydroxyl may significantly enhance the nuclease resistance of the siRNAs in tissue culture medium.

Furthermore, the siRNAs of the present invention may include modifications to the sugar-phosphate backbone or nucleosides. These modifications can be tailored to promote selective genetic inhibition, while avoiding a general panic response reported to be generated by siRNA in some cells. In addition, modifications can be introduced in the bases to protect siRNAs from the action of one or more endogenous enzymes.

In an embodiment of the present invention, the siRNA molecule may contain at least one modified nucleotide analogue. The nucleotide analogues may be located at positions where the target-specific activity, e.g., the RNAi mediating activity is not substantially effected, e.g., in a region at the 5'-end and/or the 3'-end of the RNA molecule. Particularly, the ends may be stabilized by incorporating modified nucleotide analogues. Examples of nucleotide analogues include sugar- and/or backbone-modified ribonucleotides (e.g., include modifications to the phosphate-sugar backbone). For example, the phosphodiester linkages of natural RNA may be modified to include at least one of a nitrogen or sulfur heteroatom. In backbone-modified ribonucleotides, the phosphoester group connecting to adjacent ribonucleotides may be replaced by a modified group, e.g., a phosphothioate group. In sugar-modified ribonucleotides, the 2' OH-group may be replaced by a group selected from H, OR, R, halo, SH, SR, $NH_2$, NHR, $NR_2$ or ON, wherein R is $C_1$-$C_6$ alkyl, alkenyl or alkynyl and halo is F, Cl, Br or I.

Nucleobase-modified ribonucleotides may also be utilized, e.g., ribonucleotides containing at least one non-naturally occurring nucleobase instead of a naturally occurring nucleobase. Bases may be modified to block the activity of adenosine deaminase. Exemplary modified nucleobases include, but are not limited to, uridine and/or cytidine modified at the 5-position, 5-(2-amino)propyl uridine, 5-bromo uridine; adenosine and/or guanosines modified at the 8 position, e.g., 8-bromo guanosine; deaza nucleotides, e.g., 7-deaza-adenosine; O- and N-alkylated nucleotides, e.g., N6-methyl adenosine are suitable. It should be noted that the above modifications may be combined.

Derivatives of siRNAs may also be utilized herein. For example, cross-linking can be employed to alter the pharmacokinetics of the composition, e.g., to increase half-life in the body. Thus, the present invention includes siRNA derivatives that include siRNA having two complementary strands of nucleic acid, such that the two strands are crosslinked. The present invention also includes siRNA derivatives having a non-nucleic acid moiety conjugated to its 3' terminus (e.g., a peptide), organic compositions (e.g., a dye), or the like. Modifying siRNA derivatives in this way may improve cellular uptake or enhance cellular targeting activities of the resulting siRNA derivative as compared to the corresponding siRNA, are useful for tracing the siRNA derivative in the cell, or improve the stability of the siRNA derivative compared to the corresponding siRNA.

The siRNAs of the present invention can be enzymatically produced or totally or partially synthesized. Moreover, the siRNAs can be synthesized in vivo or in vitro. For siRNAs that are biologically synthesized, an endogenous or a cloned exogenous RNA polymerase may be used for transcription in vivo, and a cloned RNA polymerase can be used in vitro. siRNAs that are chemically or enzymatically synthesized are preferably purified prior to the introduction into the cell.

Although one hundred percent (100%) sequence identity between the siRNA and the target region is preferred in particular embodiments, it is not required to practice the invention. siRNA molecules that contain some degree of modification in the sequence can also be adequately used for the purpose of this invention. Such modifications may include, but are not limited to, mutations, deletions or insertions, whether spontaneously occurring or intentionally introduced.

Moreover, not all positions of a siRNA contribute equally to target recognition. In certain embodiments, for example, mismatches in the center of the siRNA may be critical and could essentially abolish target RNA cleavage. In other embodiments, the 3' nucleotides of the siRNA do not contribute significantly to specificity of the target recognition. In particular, residues 3' of the siRNA sequence which is complementary to the target RNA (e.g., the guide sequence) may not critical for target RNA cleavage.

Sequence identity may be determined by sequence comparison and alignment algorithms known to those of ordinary skill in the art. To determine the percent identity of two nucleic acid sequences (or of two amino acid sequences), the sequences are aligned for optimal comparison purposes (e.g., gaps can be introduced in the first sequence or second sequence for optimal alignment). The nucleotides (or amino acid residues) at corresponding nucleotide (or amino acid) positions are then compared. When a position in the first sequence is occupied by the same residue as the corresponding position in the second sequence, then the molecules are identical at that position. The percent identity between the two sequences is a function of the number of identical positions shared by the sequences (e.g., % homology=# of identical positions/total # of positions×100), optionally penalizing the score for the number of gaps introduced and/or length of gaps introduced.

The comparison of sequences and determination of percent identity between two sequences can be accomplished using a mathematical algorithm. In one embodiment, the alignment generated over a certain portion of the sequence aligned having sufficient identity but not over portions having low degree of identity (e.g., a local alignment). A non-limiting example of a local alignment algorithm utilized for the comparison of sequences is the algorithm of Karlin and Altschul, 87 PROC. NATL. ACAD. SCI. USA 2264-68 (1990), and as modified as in Karlin and Altschul 90 PROC. NATL. ACAD. SCI. USA 5873-77 (1993). Such an algorithm is incorporated into the BLAST programs (version 2.0) of Altschul, et al., 215 J. MOL. BIOL. 403-10 (1990).

In another embodiment, the alignment may optimized by introducing appropriate gaps and determining percent identity over the length of the aligned sequences (e.g., a gapped alignment). To obtain gapped alignments for comparison purposes, Gapped BLAST can be utilized as described in Altschul et al., 25(17) NUCLEIC ACIDS RES. 3389-3402 (1997). In another embodiment, the alignment may be optimized by introducing appropriate gaps and determining percent identity over the entire length of the sequences aligned (e.g., a global alignment). A non-limiting example of a mathematical algorithm utilized for the global comparison of sequences is the algorithm of Myers and Miller, CABIOS (1989). Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used.

In particular embodiments, greater than 90% sequence identity, e.g., 91%, 92%, 93%, 94%, 95%, 96%, 97%, 98%, 99% or even 100% sequence identity, between the siRNA and the portion of the target gene may be used. Alternatively, the siRNA may be defined functionally as a nucleotide sequence (or oligonucleotide sequence) that is capable of hybridizing with a portion of the target gene transcript (e.g., 400 mM NaCl, 40 mM PIPES pH 6.4, 1 mM EDTA, 50° C. or 70° C. hybridization for 12-16 hours; followed by washing). Additional hybridization conditions include, but are not limited to, hybridization at 70° C. in 1×SSC or 50° C. in 1×SSC, 50% formamide followed by washing at 70° C. in 0.3×SSC or hybridization at 70° C. in 4×SSC or 50° C. 4×SSC, 50% formamide followed by washing at 67° C. in 1×SSC. The hybridization temperature for hybrids anticipated to be less than 50 base pairs in length can be about 5-10° C. less than the melting temperature (Tm) of the hybrid, where Tm is determined according to the following equations. For hybrids less than 18 base pairs in length, Tm(° C.)=2(# of A+T bases)+4(# of G+C bases). For hybrids between 18 and 49 base pairs in length, Tm(° C.)=81.5+16.6(log 10[$Na^+$])+0.41(% G+C)−(600/N), where N is the number of bases in the hybrid, and [$Na^+$] is the concentration of sodium ions in the hybridization buffer ([$Na^+$] for 1×SSC=0.165 M). Additional examples of stringency conditions for polynucleotide hybridization are provided in Sambrook, J., E. F. Fritsch, and T. Maniatis, 1989, Molecular Cloning: A Laboratory Manual, Cold Spring Harbor Laboratory Press, Cold Spring Harbor, N.Y., chapters 9 and 11, and Current Protocols in Molecular Biology, 1995, F. M. Ausubel et al, eds., John Wiley & Sons, Inc., sections 2.10 and 6.3-6.4, incorporated herein by reference. The length of the identical nucleotide sequences may be at least about 10, 12, 15, 17, 20, 22, 25, 27, 30, 32, 35, 37, 40, 42, 45, 47 50 or more bases.

2. Other Compositions for Targeting ALK DNA or mRNA

Antisense molecules can act in various stages of transcription, splicing and translation to block the expression of a target gene. Without being limited by theory, antisense molecules can inhibit the expression of a target gene by inhibiting transcription initiation by forming a triple strand, inhibiting transcription initiation by forming a hybrid at an RNA polymerase binding site impeding transcription by hybridizing with an RNA molecule being synthesized, repressing splicing by hybridizing at the junction of an exon and an intron or at the spliceosome formation site, blocking the translocation of an mRNA from nucleus to cytoplasm by hybridization, repressing translation by hybridizing at the translation initiation factor binding site or ribosome biding site, inhibiting peptide chain elongation by hybridizing with the coding region or polysome binding site of an mRNA, or repressing gene expression by hybridizing at the sites of interaction between nucleic acids and proteins. An example of an antisense oligonucleotide of the present invention is a cDNA that, when introduced into a cell, transcribes into an RNA molecule having a sequence complementary to at least part of the ALK mRNA.

Furthermore, antisense oligonucleotides of the present invention include oligonucleotides having modified sugar-phosphodiester backbones or other sugar linkages, which can provide stability against endonuclease attacks. The present invention also encompasses antisense oligonucleotides that are covalently attached to an organic or other moiety that increase their affinity for a target nucleic acid sequence. For example, intercalating agents, alkylating agents, and metal complexes can be also attached to the antisense oligonucleotides of the present invention to modify their binding specificities.

The present invention also provides ribozymes as a tool to inhibit ALK expression. Ribozymes are enzymatic RNA molecules capable of catalyzing the specific cleavage of RNA. The characteristics of ribozymes are well-known in the art. See, e.g., Rossi, 4 CURRENT BIOLOGY 469-71 (1994). Without being limited by theory, the mechanism of ribozyme action involves sequence specific hybridization of the ribozyme molecule to complementary target RNA, followed by an endonucleolytic cleavage. In particular embodiments, the ribozyme molecules include one or more sequences complementary to the target gene mRNA, and include the well known catalytic sequence responsible for mRNA cleavage. See U.S. Pat. No. 5,093,216. Using the known sequence of the target ALK mRNA, a restriction enzyme-like ribozyme can be prepared using standard techniques.

The expression of the ALK gene can also be inhibited by using triple helix formation. Nucleic acid molecules to be used in triple helix formation for the inhibition of transcription can be single stranded and composed of deoxynucleotides. The base composition of these oligonucleotides must be designed to promote triple helix formation via Hoogsteen base paring rules, which generally require sizeable stretches of either purines or pyrimidines to be present on one strand of a duplex. Nucleotide sequences may be pyrimidine-based, which will result in TAT and $CGC^+$ triplets across the three associated strands of the resulting triple helix. The pyrimidine-rich molecules provide base complementarity to a purine-rich region of a single strand of the duplex in a parallel orientation to that strand. In addition, nucleic acid molecules that are purine-rich, e.g., containing a stretch of G residues, may be chosen. These molecules will form a triple helix with a DNA duplex that is rich in GC pairs, in which the majority of the purine residues are located on a single strand of the targeted duplex, resulting in GGC triplets across the three strands in the triplex.

Alternatively, the potential sequences that can be targeted for triple helix formation may be increased by creating a so-called "switchback" nucleic acid molecule. Switchback molecules are synthesized in an alternating 5'-3',3'-5' manner, such that they base pair first with one strand of a duplex and then the other, eliminating the necessity for a sizeable stretch of either purines or pyrimidines to be present on one strand of a duplex.

It would be readily apparent to one of ordinary skill in the art that other methods of gene expression inhibition that selectively target ALK DNA or mRNA can also be used in connection with this invention without departing from the spirit of the invention. In a specific embodiment, using techniques known to those of ordinary skill in the art, the present invention contemplates affecting the promoter region of ALK to effectively switch off transcription.

3. Design and Production of the RNAi Compositions

One or more of the following guidelines may be used in designing the sequence of siRNA and other nucleic acids designed to bind to a target mRNA, e.g., shRNA, stRNA, antisense oligonucleotides, ribozymes, and the like, that are advantageously used in accordance with the present invention.

Beginning with the AUG start codon of the ALK gene, each AA dinucleotide sequence and the 3' adjacent 16 or more nucleotides are potential siRNA targets. In a specific embodiment, the siRNA is specific for a target region that differs by at least one base pair between the wild type and mutant allele or between splice variants. In dsRNAi, the first strand is complementary to this sequence, and the other strand identical or substantially identical to the first strand. siRNAs with lower G/C content (35-55%) may be more active than those with G/C content higher than 55%. Thus in one embodiment, the invention includes nucleic acid molecules having 35-55% G/C content. In addition, the strands of the siRNA can be paired in such a way as to have a 3' overhang of 1 to 4, e.g., 2, nucleotides. Thus in another embodiment, the nucleic acid molecules may have a 3' overhang of 2 nucleotides, such as TT. The overhanging nucleotides may be either RNA or DNA. In one embodiment, it may be desirable to choose a target region wherein the mismatch is a purine:purine mismatch.

Using any method known in the art, compare the potential targets to the appropriate genome database (human, mouse, rat, etc.) and eliminate from consideration any target sequences with significant homology to other coding sequences. One such method for such sequence homology searches is known as BLAST, which is available at National Center for Biotechnology Information website (http://www.ncbi.nih.gov). Select one or more sequences that meet the criteria for evaluation.

Another method includes selecting in the sequence of the target mRNA, a region located from about 50 to about 100 nt 3' from the start codon. In this region, search for the following sequences: AA(N19)TT or AA(N21), where N=any nucleotide. The GC content of the selected sequence should be from about 30% to about 70%, preferably about 50%. To maximize the specificity of the RNAi, it may be desirable to use the selected sequence in a search for related sequences in the genome of interest; sequences absent from other genes are preferred. The secondary structure of the target mRNA may be determined or predicted, and it may be preferable to select a region of the mRNA that has little or no secondary structure, but it should be noted that secondary structure seems to have little impact on RNAi. When possible, sequences that bind transcription and/or translation factors should be avoided, as they might competitively inhibit the binding of a siRNA, sbRNA or stRNA (as well as other antisense oligonucleotides) to the mRNA. Further general information about the design and use of siRNA may be found in "The siRNA User Guide," available at The Max-Planck-Institut fur Biophysikalishe Chemie website (http://www.mpibpc.mpg.de).

Negative control siRNAs should have the same nucleotide composition as the selected siRNA, but without significant sequence complementarity to the appropriate genome. Such negative controls may be designed by randomly scrambling the nucleotide sequence of the selected siRNA; a homology search can be performed to ensure that the negative control lacks homology to any other gene in the appropriate gnome.

4. Delivery of ALK RNA Targeting Compositions

Delivery of the compositions of the present invention (e.g., siRNAs, antisense oligonucleotides, or other compositions described herein) into a patient can either be direct, e.g., the patient is directly exposed to the compositions of the present invention or compound-carrying vector, or indirect, e.g., cells are first transformed with the compositions of this invention in vitro, then transplanted into the patient for cell replacement therapy. These two approaches are known as in vivo and ex vivo therapy, respectively.

In the case of in vivo therapy, the compositions of the present invention are directly administered in vivo, where they are expressed to produce the encoded product. This can be accomplished by any of numerous methods known in the art, e.g., by constructing them as part of an appropriate nucleic acid expression vector and administering them so that they become intracellular, by infection using a defective or attenuated retroviral or other viral vector, by direct injection of naked DNA, by coating with lipids or cell-surface receptors or transfecting agents, encapsulation in liposomes, nanoparticles, microparticles, or microcapsules, by administering them in linkage to a peptide which is known to enter the cell or nucleus, or by administering them in linkage to a ligand subject to receptor-mediated endocytosis which can be used to target cell types specifically expressing the receptors. Further, the compositions of the present invention can be targeted in vivo for cell specific uptake and expression, by targeting a specific receptor. See, e.g., WO93/14188, WO 93/20221, WO 92/22635, WO92/20316, and WO 92/06180.

Ex vivo therapy involves transferring the compositions of the present invention to cells in tissue culture by methods well-known in the art such as electroporation, transfection, lipofection, microinjection, calcium phosphate mediated transfection, cell fusion, chromosome-mediated gene transfer, microcell-mediated gene transfer, spheroplast fusion, and infection with a viral vector containing the nucleic acid sequences. These techniques should provide for the stable transfer of the compositions of this invention to the cell, so that they are expressible by the cell and preferably heritable and expressible by its cell progeny. In particular embodiments, the method of transfer includes the transfer of a selectable marker to the cells. The cells are then placed under selection to isolate those cells that have taken up and are expressing the transferred compositions. The resulting recombinant cells can be delivered to a patient by various methods known in the art. Examples of the delivery methods include, but are not limited to, subcutaneous injection, skin graft, and intravenous injection.

B. ALK Vaccines

Not only are ALK fusion proteins required for the development of anaplastic large cell lymphoma (ALCL), they are also antigenic: patients with ALCL mount ALK specific T- and B-cell responses. These two characteristics make ALK a unique target for vaccine therapy. Inghirami and co-workers vaccinated BALB/c mice with a DNA plasmid which coded for a large portion of the intracytoplasmic domain of ALK. Mice were then treated with syngeneic ALK positive lymphoma cells. Untreated mice developed lymphoma, while ALK-vaccinated mice did not in another study, mice were pretreated with a low tumor load of lymphoma cells. Administration of the ALK vaccine provided protection to these mice as well. Combination therapy with chemotherapeutics provided an additional benefit. See Chiarle et al., 14(6) Nat. Med. 676-80 (2009); EP2042191; Mastini et al., 87(7) J. Mol. Med. 669-77 (2009); and WO2004096142.

Without further elaboration, it is believed that one skilled in the art, using the preceding description, can utilize the present invention to the fullest extent. The following examples are illustrative only and not limiting of the remainder of the disclosure in any way whatsoever.

EXAMPLES

The following examples are put forth so as to provide those of ordinary skill in the art with a complete disclosure and description of how the compounds, compositions, articles, devices, and/or methods described and claimed herein are made and evaluated, and are intended to be purely illustrative and are not intended to limit the scope of what the inventors regard as their invention. Efforts have been made to ensure accuracy with respect to numbers (e.g., amounts, temperature, etc.) but some errors and deviations should be accounted for herein. Unless indicated otherwise, parts are parts by weight, temperature is in degrees Celsius or is at ambient temperature, and pressure is at or near atmospheric. There are numerous variations and combinations of reaction conditions, e.g., component concentrations, desired solvents, solvent mixtures, temperatures, pressures and other reaction ranges and conditions that can be used to optimize the product purity and yield obtained from the described process. Only reasonable and routine experimentation will be required to optimize such process conditions.

Materials and Methods

Tumor Samples, Cell Lines, and DNA Isolation.

A large number of human tumor samples, as indicated in the Results below, and human thyroid cancer cell lines K1, BCPAP, K5, FTC133, OCUT-1, OCUT-2, FB-1, SW1736, HTh7, HTh74, KAT18, and C643 (with the later 8 cell lines being derived from ATC), melanoma cell lines M14, A375, and UACC62, and colon carcinoma cell lines T84, RKO, and HT-29 were used for mutational analysis of the ALK gene. The original sources of the cell lines used in this study were as follows: K1 and K5 from Dr. David Wynford-Thomas (University of Wales College of Medicine, Cardiff, UK); BCPAP from Dr. Massimo Santoro (University of Federico H, Naples, Italy); FTC133 from Dr. Georg Brabant (University of Manchester, Manchester, UK); OCUT-1 and OCUT-2 from Dr. Naoyoshi Onoda (Osaka City University Graduate School of Medicine, Osaka, Japan); KAT18 from Dr. Kenneth B. Ain (University of Kentucky Medical Center, Lexington, Ky.); FB-1 from Dr. Riccardo Giannini (Department of Surgery, University of Pisa, Pisa, Italy); SW1736, HTh7, HTh74, and C643 from Dr. N. E. Heldin (University of Uppsala, Uppsala, Sweden). These cell lines have recently been tested and authenticated to be distinct thyroid cancer cell lines (17). The melanoma cell lines UACC62 and M14 were obtained from the cell bank of National Cancer Institute (Bethesda, Md.), and the melanoma cell line A375 and the colon cancer cell lines T84, RKO, and HT-29 were obtained from American Type Culture Collection (ATCC). Use of tumor samples was Institutional Review Board approved as reported previously (18). Except for FTC133 cells cultured in DMEM/Ham's F-12 medium, all tumor cell lines were cultured in RPMI-1640 medium, supplemented with 10% FBS, 2 mmol/L Lglutamine, streptomycin (100 mg/mL), and penicillin (100 U/mL). Genomic DNA (from cell lines and tumors) was isolated by phenol-chloroform extraction, using MaXtract high-density gel tubes (Qiagen) as described previously (19).

PCR Amplification and Sequencing.

PCR amplification of exons 23, 24, and 25 of the ALK gene was conducted using the primers and conditions as described previously (10) (ALK ex 23: Forward primer AAGATTTGCCCAGACTCAGC (SEQ ID NO:8); Reverse primer TGTCCTTGGCACAACAACTG (SEQ NO:9)). The amplified PCR products were directly sequenced using a BigDye terminator v3.1 cycle sequencing ready reaction kit (Applied Biosystems) and an ABI PRISM 3730 automated next generation genetic analyzer (Applied Biosystems), GenBank accession number for ALK is NM_004304.3 (SEQ ID NO:6).

Multiple Amino Acid Sequence Alignment.

Original amino acid sequences ALK of various species were obtained from NCBI database (http://www.ncbi.nlm.nih.gov/protein/) as follows: *H_sapiens* (NP_004295.2) (SEQ ID NO:7), *C_lupus* (XP_540136.2), *B_taurus* (XP_616782.3), *M_musculus* (NP_031465.2), *G_gallus* (XP_419364.2), and *D_rerio* (XP_691964.2). These amino acid sequences were compared using a computer-based multiple sequence alignment program (http://pir.georgetown.edu/pirwww/search/multialn.shtml).

Expression Vectors and Site-Directed Mutagenesis.

The expression vector pcDNA3 carrying wild-type ALK and mutant ALKs (K1062M and F1174L) are a kind gift from Profs. Yasuhide Hayashi and Seishi Ogawa at The University of Tokyo, Tokyo, Japan (10). The expression vector pcDNA3 carrying wild-type ALK was used to generate the novel ALK mutants L1198F and G1201E discovered in the present study with a Quick Change XL II Site-Directed mutagenesis kit (Stratagene) according to the instructions of the manufacturer. The primers were designed using a template-specific mutagenic primer design program. The primer sequences are as follows: for L1198F: sense, ALK-C3592T_F 5'-CATCCTGCTGGAGTTCATGGCGGGGGG-3' (SEQ NO:1); antisense, ALK-C3-592T_R 5'-CCCCCCGCCATGAACTCCAGCAGGATG-3' (SEQ ID NO:2). For G1201E; sense, ALK-G3602A_F 5'-GAGCTCATGGCGGAGGGAGACCTCAAG-3' (SEQ ID NO:3); and antisense, ALK-G3602A_R 5'-CTTGAGGTCTCCCTCCGCCATGAGCTC-3' (SEQ ID NO:4). The mutations were confirmed in the vectors by sequencing with the primer ALKVEC_F 5'-TCTCGCTGTGGTGACCTCTG-3' (SEQ ID NO:5). Plasmid DNAs for the transfection experiments were purified using a mini prep kit (catalogue no. K2100-11; Invitrogen).

Cell Culture, Transfection, and Pooled Stable Expression.

NIH3T3 cells (ATCC) were grown in DMEM and supplemented with fetal calf serum and plated ($8.0\times10^5$ cells/well) on 6-well plates, Twenty-four hours later, cells were transfected using the Lipofectamine 2000 Transfection Reagent (Invitrogen) with equal amount of empty vector or vector containing wild-type ALK or mutant ALK DNA per manufacturer's instructions. Cells were selected using 800 mg/mL G418 (Stratagene) 48 hours after transfection. Medium was changed after every 3 days, After 14 days of selection, stably formed clones were pooled and integration of the plasmid was checked by PCR and expression of the ALK protein was confirmed by Western blotting. Stably transfected pooled clones were used for functional studies.

ALK Kinase Assay.

The ALK tyrosine kinase assay was a non-radioactive solid phase ELISA, which was conducted as described previously (10) using the Universal Tyrosine Kinase Assay Kit (catalogue no. MK410: Takara Bio Inc.). Briefly, cells stably transfected with empty vector, wild-type ALK, the 2 novel ALK mutants (L1198F and G1201E), and the 2 positive ALK mutant controls (K1062M and F1174L) were lysed and lysates were centrifuged at 12,000×g for 10 minutes at 4° C., The supernatants were collected, and protein concentration was measured using a DC protein assay kit (Bio-Rad Laboratories). For each enzymatic reaction, an equal volume a cell lysate containing the same amount of protein was added to the kinase reaction buffer and the mixture was transferred to the microplate supplemented with the kit containing the substrate [immobilized peptide poly(Glu-Tyr)]. The kinase reaction was initiated by adding 40 mmol/L ATP-2Na solution, followed by incubation for 20 minutes at room temperature.

Western Blotting.

Western blotting was done as described previously (20). Briefly, 15 mg of cell lysate proteins prepared for ALK kinase assay was separated on SDS-PAGE and transferred to polyvinylidene difluoride membrane (Millipore Co). After transfer, the membrane was blocked with 5% skim-milk/PBS containing 0.1% Tween 20 (PBST) for 1 hour at room temperature and the membrane was sliced on the basis of the molecular weight and incubated with primary antibodies. Membranes were incubated overnight at 4° C. with anti-Flag (catalogue no. 2368; Cell Signaling Technology), anti-phospho-Akt (catalogue no. sc-7985; Santa Cruz Biotechnology), or anti-phospho-ERK (catalogue no. sc-7383; Santa Cruz Biotechnology) primary antibodies. Membranes were incubated with anti-Akt (catalogue no. sc-8312), anti-ERK (catalogue no. sc-94), or antib-actin (catalogue no. sc-1616; Santa Cruz Biotechnology) primary antibodies for 1 hour at room temperature. After washing 4 times with PBST, blots were incubated with respective horseradish peroxidase-conjugated secondary antibodies (catalogue nos. sc-2004 and sc-2005; Santa Cruz Biotechnology) for 1 hour at room temperature. After washing with PBST, protein bands on the membrane were detected with enhanced chemiluminescence reaction and exposure to X-ray films.

Cell Focus Formation Assay.

Cell focus formation assay was conducted as described previously (21). Briefly, NIH3T3 cells were transfected with equal amount of empty vector, wild-type, or each of mutant ALK expression vectors, using the Lipofectamine 2000 transfection reagent following the manufacturer's instructions (Invitrogen Life Technologies). Twenty-four hours after the transfection, cells were selected using G418 (800 mg/mL) for 7 days. Selected cells were trypsinized, pooled, and plated ($5\times10^5$ cells) on 6-well plates. Medium was changed every 3 to 4 days. After 14 days, the number of morphologically transformed foci was counted and photographed (Zeiss Axiovert 200M).

Soft Agar Colony Formation Assay.

Soft agar colony formation assay was conducted as previously described (10). Briefly, NIH3T3 cells stably expressing vector, wild-type, or mutant ALKs were seeded ($1.0\times10^4$ cells) on 6-well plates (Costar; Corning) in 0.3% agar (catalogue no. 214010; BD Biosciences) over a bottom layer of 0.6% agar. After 4 weeks, the colonies of greater than 0.1 mm diameter were counted and photographed (Zeiss Axiovert 200M; Carl Zeiss).

Invasion Assay.

Cell invasion assay was conducted as described previously (20). Briefly, the assay was conducted using Matrigel invasion chambers consisting of BD Falcon cell culture inserts containing a polyethylene terephthalate (PET) membrane with 8-mm pores coated with Matrigel matrix (BD BioCoat Matrigel Invasion Chamber; BD Biosciences). Cells expressing the vector, wild-type, or mutant ALK were completely serum starved for 7 to 8 hours and then collected and resuspended ($5\times10^4$ cells) in 500 mL of serum-free DMEM with 0.1% bovine serum albumin. Culture inserts were placed in the wells of a BD Falcon 24-well multiwell companion plate, and 750 mL of DMEM containing 1% serum was added to the lower compartment of each well. Cell suspensions were added to each culture inserts. After a 22-hour incubation at 37° C. with 5% CO2, the noninvading cells on top of the Matrigel were removed using cotton swab and invaded cells on the lower side of the membrane were fixed with 70% ethanol and stained with Coomassie Brilliant Blue. Invading cells were counted and photographed under a microscope with 10× magnification (Nikon Eclipse ME-600-DS-5M-L1). All the data of assays presented represent at least 2 similar experiments.

Results

Example 1

Identification of Novel Somatic ALK Mutations in ATC

The tyrosine kinase domain exons 23 and 25 of the ALK gene were analyzed for mutation in 12 thyroid cancer cell lines (including 8 ATC cell lines), 36 PTCs (including 12 cases of each conventional, follicular variant, and tall cell PTC), 20 FTCs, and 18 ATC tumor samples. These exons were chosen for analysis because they contained the hot spots for ALK mutations found in neuroblastomas. No mutation was found in the thyroid cancer cell lines as well as in the PTC and FTC tumor samples. However, 2 novel missense heterozygous ALK point mutations were found in ATC tumor samples. As shown in FIG. 1A, a mutation found in a case of ATC represented a C>T transition in nucleotide position 3,592. This mutation changed codon 1,198 from CTC to TTC, resulting in the amino acid change from lysine to phenylalanine (L1198F) of ALK. As shown also in FIG. 1A, the other mutation found in another case of ATC represented a G>A transition in nucleotide position 3,602. This mutation changed codon 1,201 from GGG to GAG, resulting in the amino acid change of glycine to glutamic acid (G1201E) of ALK. Reverse sequencing using antisense primers confirmed these 2 mutations (FIG. 1A). The matched normal tissues in these 2 cases showed the wild-type ALK gene (FIG. 1A), suggesting that the novel ALK mutations identified in the ATC samples were somatic mutations. These mutations were not found in COSMIC Catalog Of Somatic Mutations In Cancer, a database of Sanger Institute, UK (http://www.sanger.ac.uk/genetics/CGP/cosmic/), and in the literature. The databases of single-nucleotide polymorphism were also checked, including the major Web sites of Ensembl (http://uswest.ensembl.org) and NCBI (http://www.ncbi.nlm.nih- .gov/projects/SNP/), and did not find germ line variations that represented these ALK mutations. Therefore, this is the first report of these somatic mutations of the ALK gene in human cancers. Exon 24 of the ALK gene was also examined in the ATC samples but no mutations were found. In these ATC tumors, ALK mutations that had been previously reported in neuroblastomas were not found. The prevalence of ALK mutations in ATC in the present study was 11.11% (2 of 18).

Exons 23 and 25 of the ALK gene were also analyzed in 3 melanoma cell lines, 3 colon carcinoma cell lines, 44 melanomas, and 47 colon carcinoma samples. The ALK mutation was not found in any of these samples, suggesting that ALK mutation is not a common event in these cancers. A few silent mutations were found in these cancers (data not shown).

Example 2

Figures 1B, 1C:
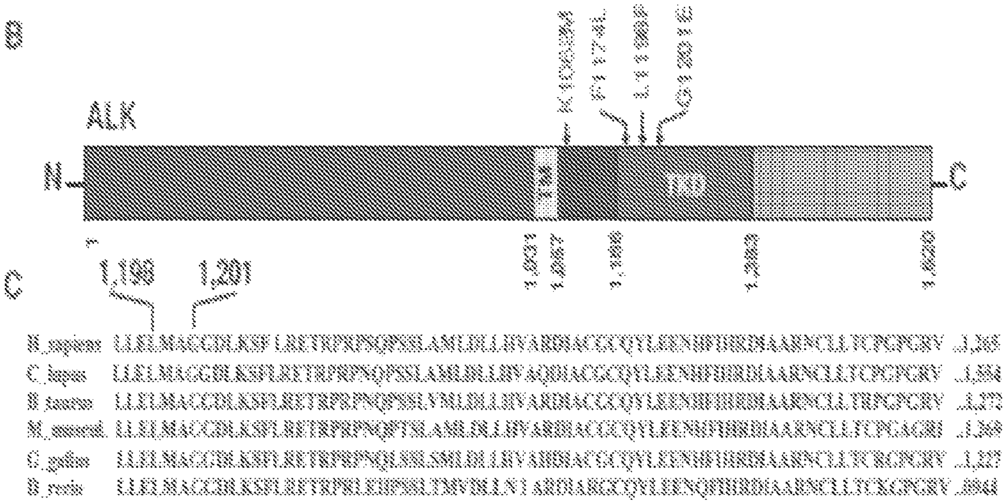
FIG. 1B is a schematic diagram of the ALK. Shown are the relative positions of the novel somatic ALK mutations L1198F and G1201E and the previously characterized mutations K1062M and F1174L from neuroblastoma. L1198F and G1201E are located in the tyrosine kinase domain of the ALK.
FIG. 1C is an amino acid sequence alignment of the ALK proteins from 6 species. Shown are the L1198 and G1201 residues that are evolutionarily completely conserved among these different species. Numbers indicate amino acid or codon positions. Amino acid sequences are numbered with the initiation codon (methionine) of each protein defined as number 1.
Figure 2A:
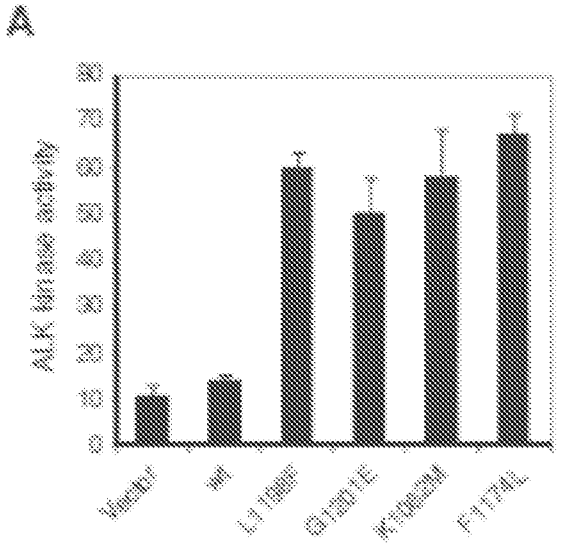
FIG. 2A shows the results of an in vitro assay of tyrosine kinase activities of ALK mutants. NIH3T3 cells stably expressing Flag-tagged vector, wild-type ALK (wt-ALK), and each of ALK mutants as indicated were lysed. The cell lysates were assayed for tyrosine kinase activity as described in the Materials and Methods. The enzymatic activities were expressed as measured optical density value ×20. Results represent mean±SD of 3 independent experiments.
Figure 2B:
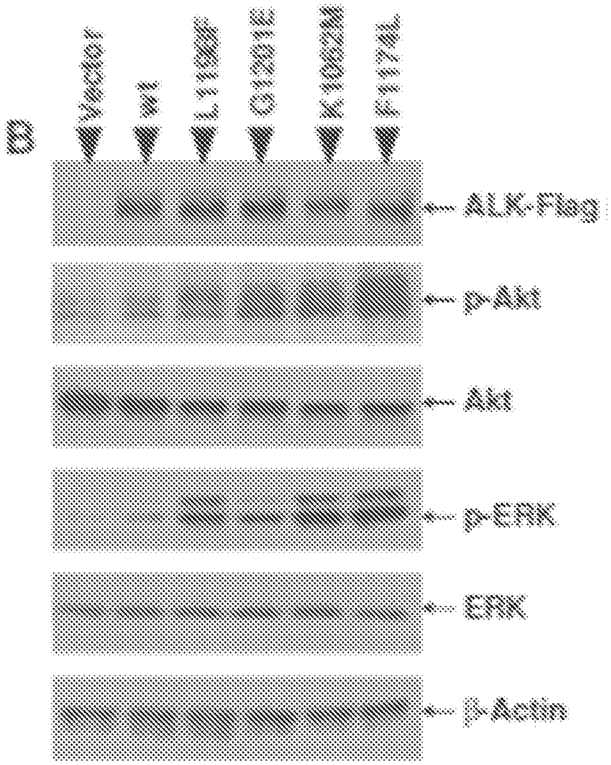
FIG. 2B shows the activation of the PI3K/Akt and MAP kinase pathways. This is reflected by increased phosphorylation of Akt (p-Akt) and phosphorylation of ERK (p-ERK), respectively. NIH3T3 cells stably transfected with the indicated vector constructs, as described in FIG. 1A cell lysate proteins, were subjected to Western blot analyses for the indicated proteins by using appropriate antibodies as described in Materials and Methods. Successful protein expression of Flag-tagged wild-type ALK and each of the ALK mutants is shown in the top row of FIG. 1B. The key molecules of the 2 pathways are shown in the subsequent rows. Total Akt, ERK, and b-actin were used for quality control of loading proteins.

Increased Tyrosine Kinase Activities of Novel Somatic ALK Mutants L1198F and G1201E and Their Activation of the PI3K/Akt and MAP Kinase Pathways As shown in FIG. 1B, the somatically mutated amino acid residues L1198F and G1201E are located within the tyrosine kinase domain (amino acids 1,057-1,383) of the ALK protein. Moreover, as shown in FIG. 1C, alignment comparison of amino acid sequences of ALK proteins from 6 different species revealed that the L1198 and G1201 residues were evolutionarily conserved residues of the ALK proteins among various species. These novel somatic ALK mutations likely altered the tyrosine kinase activity of ALK. To test this idea, in vitro mutagenesis was conducted to generate these 2 mutations and tested their tyrosine kinase activities. To this end, NIH3T3 cells stably expressing vector, wild-type, and each mutant ALK were lysed and assayed for in vitro tyrosine kinase activities. As shown in FIG. 2A, the novel ALK mutants L1198F and G1201E displayed dramatically increased tyrosine kinase activities compared with the wild-type ALK. The neuroblastoma-associated ALK mutants K1062M and F1174L, as positive controls in the assay, also displayed high activities as expected (FIG. 2A). Western blot analysis confirmed the corresponding protein expression of the expression vector constructs (FIG. 2B, top). These results showed that the 2 novel ALK mutations found in ATC are gain of function mutations.

As oncogenic fusion ALK proteins were previously shown to activate the PI3K/Akt and MAP kinase pathways (8, 9), whether the novel ALK mutants discovered in this study had any impact on the signaling of these 2 pathways was tested next. As shown in FIG. 2B, compared with wild-type ALK, phosphorylation of both Akt and ERK was elevated in NIH3T3 cells expressing the mutant L1198F or G1201E, similar to ALK mutants K1062M and F1174L tested here as positive controls. This was consistent with high immunostaining scores for the phosphorylation levels of Akt and ERK in the 2 cases of ATC harboring the ALK mutations, which were revealed in a previous study of ours (19). Thus, the role of the 2 novel ALK mutations in the tumorigenesis of ATC likely involves aberrant activation of the PI3K/Akt and MAP kinase pathways.

Example 3

Figure 3A:
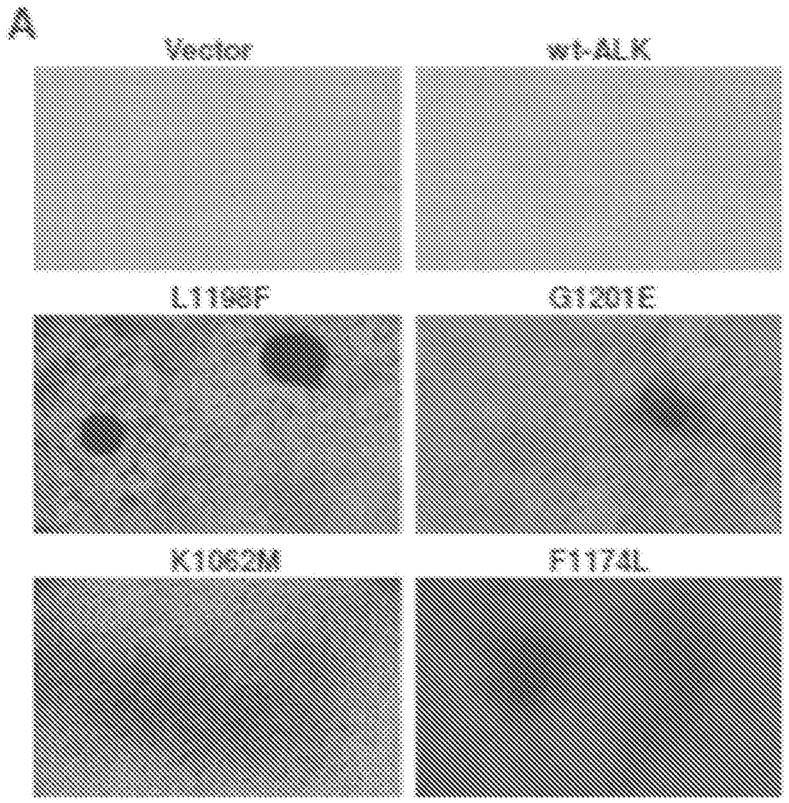
FIG. 3A shows the cell focus-forming activities of ALK mutants. Shown are images of adherent growth of NIH3T3 cells transfected with Flag-tagged vector, wild-type ALK (wt-ALK), and each of the ALK mutants indicated. Cells were cultured in regular medium with 10% fetal calf serum under standard conditions. Images of cell foci were photographed with 10× magnification after appropriate culture of cells as described in the Materials and Methods.
Figure 3B:
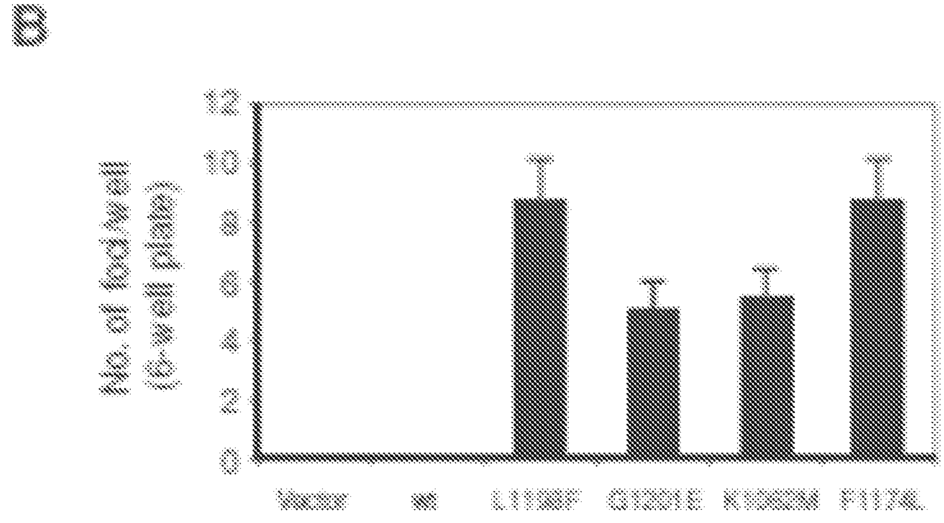
FIG. 3B shows the number of cell foci formed with the indicated transfections. The number of transformed foci was counted 14 days after cell transfection. Results represent mean±SD of 3 independent experiments.

Novel Somatic ALK Mutants L1198F and G1201E Promoted Cell Transformation and Invasion Given the known cell-transforming abilities of fusion ALK proteins and neuroblastoma-associated ALK mutants (10), the transforming abilities of the 2 novel ALK mutants L1198F and G1201E was examined to functionally test their oncogenic potential. To this end, NIH3T3 cells were transfected with empty vector, wild-type ALK, and various ALK mutants and examined their ability to form cell focus and anchorage-independent colonies. As shown in FIG. 3A, cells expressing ALK mutants L1198F and G1201E lost cell contact-mediated growth inhibition and grew foci of multilayers of cells whereas control cells (vector and wild-type ALK) exhibited contact inhibition and grew in monolayer of cells. Moreover, ALK mutants L1198F and G1201E were also associated with a much larger number of foci of multilayers of cells than the wild-type ALK (FIG. 3B). As a positive control, the previously well-characterized neuroblastoma-associated ALK mutants K1062M and F1174L showed similar cell focus-forming abilities (FIGS. 3A and B).

Anchorage-independent growth on soft agar also reflects a transformation property of cells. As shown in FIG. 3C, like the positive control ALK mutants K1062M and F1174L, the novel ALK mutants L1198F and G1201E induced the formation of much larger cell colonies on soft agar than that by vector and wild-type ALK. The number of large cell colonies induced by these mutants was also much bigger than that of the vector and the wild-type ALK (FIG. 3D).

Figure 4A:
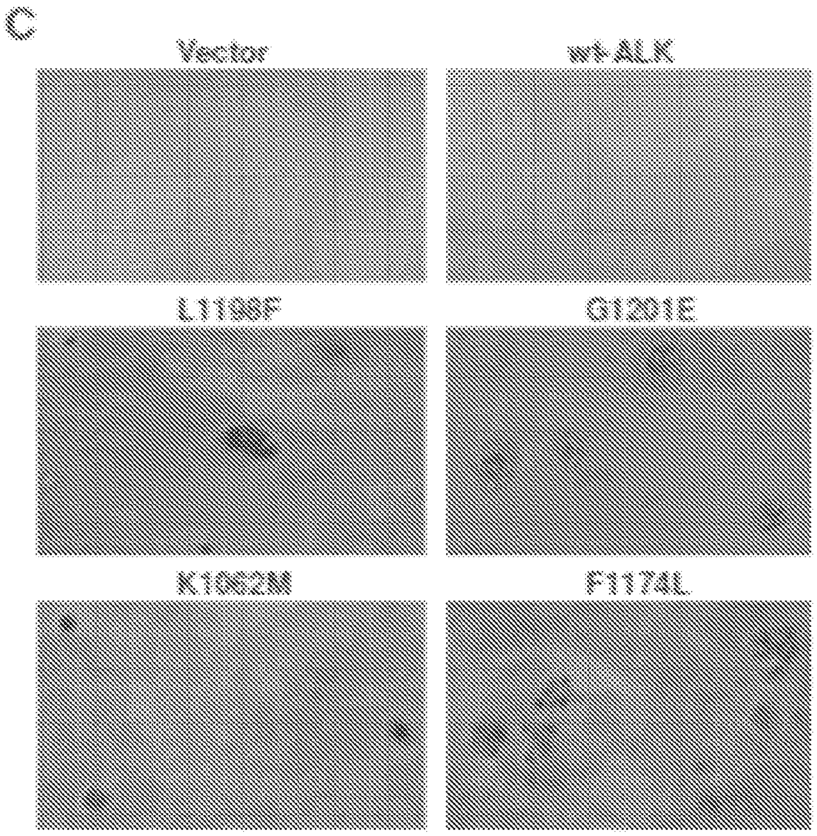
FIG. 4A shows the results from the in vitro invasion assay of NIH3T3 cells with various transfections. Cells transfected with Flag-tagged vector, wild-type ALK (wt-ALK), and each construct of the indicated ALK mutants. Cell invasion assay was conducted as described in Materials and Methods. Shown are the cells that invaded on the Matrigel matrix-coated polyethylene terephthalate (PET) membrane after removal of the noninvasive cells.
Figure 4B:
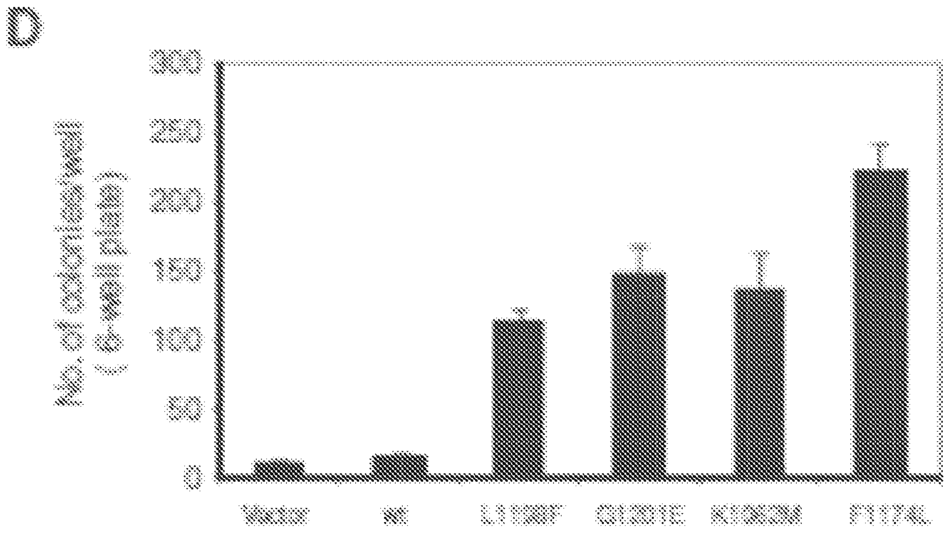
FIG. 4B shows the number of invasive cells with the indicated transfections. Results of each column represent the mean±SD of the numbers of invasive cells from 3 independent experiments.

An earlier study showed cell invasion-promoting properties of various fusion ALK proteins (22). Such properties of the ALK mutants L1198F and G1201E were tested in the present studies. As shown in FIG. 4A, like ALK K1062M and F1174L, NIH3T3 cells transfected with the 2 novel ALK mutants were much more invasive on Matrigel matrix-coated membranes than vector or wild-type ALK-transfected cells. The number of invading cells was much bigger with the ALK mutants than with the vector and wild-type ALK (FIG. 4B).

Discussion

For the first time the ALK gene was analyzed for mutations in tumors other than neuroblastomas and 2 somatic novel missense ALK point mutations, C3592T and G3602A, were identified in ATC. The 2 mutations caused amino acid change from lysine to phenylalanine (L1198F) and from glycine to glutamic acid (G1201E) of ALK, respectively. They are both in exon 23 and only 3 codons apart, with a relatively high ALK mutation prevalence of 11% in ATC, similar to that in sporadic neuroblastomas (10-12, 14). The novel mutations L1198F and G1201E are located in the tyrosine kinase domain of the ALK. More specifically, they are in the hinge region of this domain. It has been shown that ALK binds ADP and staurosporine at the hinge region of the interlobe cleft, suggesting important specific functions of this region (23). Therefore, it may be expected that amino acid changes in this region may result in conformational change of the ALK protein, with significant functional consequences to the tyrosine kinase activity of ALK. Indeed, both mutations were shown to be gain-of-function mutations, conferring that ALK dramatically increased tyrosine kinase activities. Like several previously characterized ALK mutants in neuroblastomas, the 2 novel ALK mutants found in ATC strongly promoted cell focus formation, anchorage-independent growth, and cell invasion, effectively showing their oncogenic functions. The present inventors thus report ALK mutations in ATC with a comparable prevalence and oncogenic power with those in neuroblastomas. Expression of ALK seems to be restricted to tissues originating from neuroectodermal developmental origin (24). Thyroid cancer cells were specifically shown to express ALK (24). Thus, the mutant ALK gene can be expected to be expressed in thyroid cells, making such mutations relevant for thyroid tumorigenesis. ATC is the most aggressive type of thyroid cancer; in fact, it is one of the most rapidly developing lethal human cancers (16). With the current available treatments, patients with ATC usually die within 5 to 6 months after initial diagnosis. The finding of the ALK mutations in ATC, but not in generally indolent differentiated PTC and FTC, suggests that activating genetic alterations of the ALK gene play a role in the aggressiveness of a subgroup of ATC. This is interestingly consistent with previous observations that ALK mutations were also associated with advanced disease stages and poor outcomes of neuroblastoma (11, 12, 14).

The molecular signaling pathways mediating the oncogenic role of ALK mutations in ATC involved the PI3K/Akt and MAP kinase pathways, as suggested by the present inventors' demonstration of the coupling of the 2 novel ALK mutants to increased phosphorylation of Akt and ERK in both ALK-transfected cell lines and ATC tumor tissues. This is not surprising, as tyrosine kinases, particularly RTK, typically activate these 2 pathways. Interestingly, in neuroblastoma, ALK mutations were also shown to be coupled to PI3K/Akt and MAP kinase signaling (8, 9). Thus, it seems that coupling to these pathways is a common mechanism involved in the oncogenic role of genetic alterations of the ALK gene in human cancer. The PI3K/Akt and MAP kinase pathways play a fundamental role in thyroid tumorigenesis (25, 26). Dual activation of the 2 pathways driven by genetic alterations is a fundamental mechanism for the pathogenesis of ATC (19, 27). ALK mutations discovered in the present study add a novel set of genetic alterations that contribute to this mechanism.

Development of inhibitors targeting ALK is an exciting current research area as a novel therapeutic strategy for neuroblastomas harboring ALK mutations, ALCL NPM1-ALK, NSCLC harboring EML4-ALK, and IMT harboring TMP3/4-ALK and RANBP2-ALK fusion genes (1, 2). It has been recently reported that most of the patients with NSCLC harboring EML4-ALK responded effectively to the treatment with an anti-ALK agent, crizotinib (28), which has also been recently reported to be effective in treating a patient with IMT harboring RANBP2-ALK (29). In future studies, it will be interesting to examine the effects of this ALK inhibitor on the growth of ALK mutants in in vitro cell line assay and in in vivo animal tumor studies. This will not only test the dependence of cells or tumors on these ALK mutants but also test the therapeutic potentials of targeting these novel ALK mutants in human cancers, particularly ATC. It is therefore highly attractive to speculate that the subset of patients with ATC harboring ALK mutations may be similarly and effectively treated with this and other ALK inhibitors.

In summary, in the present study, the present inventors report novel ALK mutations in ATC with a comparable prevalence and oncogenic power to those in neuroblastomas. This is the first report on ALK mutations in non-neuroblastoma human cancers. These are gain-of-function mutations that cause dual activation of the PI3K/Akt and MAP kinase pathways in ATC. They may represent a novel therapeutic target in ATC for the recently developed ALK inhibitors.

REFERENCES

1. Kelleher F C. McDermott R. The emerging pathogenic and therapeutic importance of the anaplastic lymphoma kinase gene. Eur J Cancer 2010; 46:2357-68.
2. Ardini E, Magnaghi P, Orsini P, Galvani A, Menichincheri M. Anaplastic lymphoma kinase: role in specific tumours and development of small molecule inhibitors for cancer therapy. Cancer Lett 2010; 299:81-94.
3. Morris S W, Kirstein M N, Valentine M B, Dittmer K G, Shapiro D N, Saltman D L, et al. Fusion of a kinase gene, ALK, to a nucleolar protein gene, NPM, non-Hodgkin's lymphoma. Science 1994; 263:1281-4.
4. Soda M, Choi Y L, Enomoto M, Takada S, Yamashita Y, Ishikawa S., et al. Identification of the transforming EML4-ALK fusion gene in non small-cell lung cancer. Nature 2007; 448:561-6.
5. Ma Z, Hill D A, Collins M H, Morris S W, Sumegi J, Zhou M, et al. Fusion of ALK to the Ran-binding protein 2 (RANBP2) gene in inflammatory myofibroblastic tumor. Genes Chromosomes Cancer 2003; 37: 98-105.
6. Wellmann A, Doseeva V, Butseher W, Raffeld M, Fukushima P, Stetler-Stevenson M, et al. The activated anaplastic lymphoma kinase increases cellular proliferation and oncogene up-regulation in rat 1a fibroblasts. FASEB J 1997; 11:965-72.
7. Lange K, Uckert W, Blankenstein T, Nadrowitz R, Bittner C, Renauld J C, et al. Overexpression of NPM-ALK induces different types of malignant lymphomas in IL-9 transgenic mice. Oncogene 2003; 22: 517-27.
8. Chiarle R, Voena C, Ambrogio C, Piva R, Inghirami G. The anaplastic lymphoma kinase in the pathogenesis of cancer. Nat Rev Cancer 2008; 8:11-23.
9. Palmer R H, Vernersson E, Grabbe C, Hallberg B. Anaplastic lymphoma kinase: signaling in development and disease. Biochem J 2009; 420:345-61.
10. Chen Y, Takita J, Choi Y L, Kato M, Ohira M, Sanada M, et al. Oncogenic mutations of ALK kinase in neuroblastoma. Nature 2008; 455:971-4.
11. Caren H, Abel F, Koper P, Martinsson T. High incidence of DNA mutations and gene amplifications of the ALK gene in advanced sporadic neuroblastoma tumours. Biochem J 2008; 416:153-9.
12: George R E, Sanda T, Hanna M, Fr€ohling S, Luther W II, Zhang J, et al. Activating mutations in ALK provide a therapeutic target in neuroblastoma. Nature 2008; 455: 975-8.
13. Janoueix-Lerosey I, Lequin D, Brugieres L, Ribeiro A, de Pontual L, Combaret V, et al. Somatic and germline activating mutations of the ALK kinase receptor in neuroblastoma. Nature 2008; 455:967-70.
14. Mosse Y P, Laudenslager M, Longo L, Cole K A, Wood A, Attiyeh E F, et al. Identification of ALK as a major familial neuroblastoma predisposition gene. Nature 2008; 455:930-5.
15. Osajima-Hakomori Y, Miyake I, Ohira M, Nakagawara A, Nakagawa A, Sakai R. Biological role of anaplastic lymphoma kinase in neuroblastoma. Am J Pathol 2005; 167: 213-22.
16. Neff R L, Farrar W B, Kloos R T, Burman K D. Anaplastic thyroid cancer. Endocrinol Metab Clin North Am 2008; 37:525-38.
17. Schweppe R E, Klopper J P, Korch C, Pugazhenthi U, Benezra M, Knauf J A, et al. Deoxyribonucleic acid profiling analysis of 40 human thyroid cancer cell lines reveals cross-contamination resulting in cell line redundancy and misidentification. J Clin Endocrinol Metab 2008; 93:4331-41.
18. Murugan A K, Dong J, Xie J, Xing M. MEK1 mutations, but not ERK2 mutations, occur in melanomas and colon carcinomas, but none in thyroid carcinomas. Cell cycle 2009; 14:1056-60.
19. Liu Z, Hou P, Ji M, Guan H, Studeman K, Jensen K, et al. Highly prevalent genetic alterations in receptor tyrosine kinases and phosphatidylinositol 3-kinase/Akt and mitogen-activated protein kinase pathways in anaplastic and follicular thyroid cancers. J Clin Endocrinol Metab 2008; 93:3106-16.

20. Murugan A K, Hong N T, Fukui Y, Muniraian A K, Tsuchida N. Oncogenic mutations of the PIK3CA gene in head and neck squamous cell carcinomas. Int J Oncol 2008; 32:102-11.
21. Tao W J, Lin H, Sun T, Samanta A K, Arlinghaus R. BCR-ABL oncogenic transformation of NIH 3T3 fibroblasts requires the IL-3 receptor. Oncogene 2008; 27:3194-200.
22. Armstrong F, Duplantier M M, Trempat P, Hieblot C, Lamant L, Espinos E, et al. Differential effects of X-ALK fusion proteins on proliferation, transformation, and invasion properties of NIH3T3 cells. Oncogene 2004; 23:6071-82.
23. Lee C C, Jia Y. Li N, Sun X, Ng K, Ambing E, et al. Crystal structure of the anaplastic lymphoma kinase (ALK) catalytic domain. Biochem J 2010; 430:425-37.
24. Dirks W G, F€ ahnrich S, Lis Y, Becker E, MacLeod R A, Drexler H G. Expression and functional analysis of the anaplastic lymphoma kinase (ALK) gene in tumor cell lines. Int J Cancer 2002; 100:49-56.
25. Nikiforov Y E. Thyroid carcinoma: molecular pathways and therapeutic targets. Mod Pathol 2008; 21:S37-43.
26. Saji M, Ringel M D. The PI3K-Akt-mTOR pathway in initiation and progression of thyroid tumors. Mol Cell Endocrinol 2010; 321:20-8.
27. Xing M. Genetic alterations in the phosphatidylinositol-3 kinase/Akt pathway in thyroid cancer. Thyroid 2010; 20:697-706.
28. Kwak E L, Bang Y J, Camidge D R, Shaw A T, Solomon B, Maki R G, et al. Anaplastic lymphoma kinase inhibition in non-small-cell lung cancer. N Engl J Med 2010; 363:1693-703.
29. Butrynski J E, D'Adamo D R, Hornick J L, Dal Cin P, Antonescu C R, Jhanwar S C, et al. Crizotinib in ALK-rearranged inflammatory myofibroblastie tumor. N Engl J Med 2010; 363:1727-33.

That which is claimed is:

1. A method for treating an anaplastic thyroid cancer (ATC) in a patient suffering thereform comprising the step of administering to the patient an effective amount of an anaplastic lymphoma kinase (ALK) inhibitor.

2. The method of claim 1, wherein the ALK inhibitor is crizotinib.

3. The method of claim 1, wherein the patient has a C3592T mutation in exon 23 of the ALK gene.

4. The method of claim 1, wherein the patient has a G3602A mutation in exon 23 of the ALK gene.

5. The method of claim 1, further comprising the step of determining whether the patient has a C3592T and/or a G3602A mutation in exon 23 of the ALK gene prior to the administering step.

6. A method for treating ATC in a thyroid cancer patient comprising the steps of:

a. determining whether the thyroid cancer patient has a C3592T and/or a G3602A mutation in exon 23 of the anaplastic lymphoma kinase (ALK) gene; and b. treating the patient with an ALK inhibitor therapy if the patient has either or both of the mutations.

7. A method for treating anaplastic thyroid cancer (ATC) in a thyroid cancer patient comprising the step of treating the patient with an ALK inhibitor therapy if the thyroid cancer patient has a C3592T and/or a G3602A mutation in exon 23 of the ALK gene.

8. The method of claim 6, wherein the ALK inhibitor is crizotinib.

9. A method for treating a cancer patient comprising the step of administering to the patient an effective amount of an ALK inhibitor, wherein the cancer patient has a C3592T and/or a G3602A mutation in exon 23 of the ALK gene.

10. A method for treating a cancer patient comprising the steps of:

a. determining whether the cancer patient has a C3592T mutation in exon 23 of the anaplastic lymphoma kinase (ALK) gene; and b. treating the patient with an ALK inhibitor therapy if the patient has either or both of the mutations.

11. The method of claim 10, wherein the ALK inhibitor is crizotinib.

12. The method of claim 10, wherein the cancer is a neuroblastoma.

13. A method for treating a neuroblastoma cancer patient comprising the step of administering to the patient an effective amount of an ALK inhibitor, wherein the patient has a C3592T and/or a G3602A mutation in exon 23 of the ALK gene.

14. The method of claim 13, wherein the ALK inhibitor is crizotinib.

15. The method of claim 1, further comprising the step of administering an inhibitor of the PI3K/Akt pathway.

16. The method of claim 1, further comprising the step of administering an inhibitor of the MAP kinase pathway.

17. A method for treating a cancer patient comprising the step of administering to the patient an inhibitor of a protein or pathway selected from the group consisting of ALK, the PI3K/Akt pathway and the MAP kinase pathway, wherein the patient has a C3592T and/or a G3602A mutation in exon 23 of the ALK gene.

18. The method of claim 17, wherein the ALK inhibitor is crizotinib.

19. The method of claim 17, wherein the patient has ATC.

20. The method of claim 17, wherein the patient has a neuroblastoma.

21. A method for diagnosing ATC in patient comprising the step of performing an assay on a biological sample from the patient to identify the presence or absence of a C3592T and/or a G3602A mutation in exon 23 of the ALK gene according to SEQ ID NO:6, wherein the presence of either of both of the mutations correlates with a diagnosis of ATC in the patient.

22. A method for determining a patient's risk of developing ATC comprising the step of performing an assay on a biological sample from the patient to identify the presence or absence of a C3592T and/or a G3602A mutation in exon 23 of the ALK gene according to SEQ ID NO:6, wherein the presence of either of both of the mutations correlates with a prognosis that the patient has a higher risk of ATC than a patient without the mutations, and wherein the absence of the mutations correlates with a prognosis that the patient has a lower risk of ATC than a patient with either or both of the mutations.

23. A method for detecting ATC in a patient comprising the step of determining the presence of a C3592T and/or a G3602A mutation in exon 23 of the ALK gene according to SEQ ID NO:6 in a blood sample of a patient, wherein the presence of the mutation indicates ATC in the patient.

24. A method for distinguishing ATC from non-ATC samples comprising the step of determining the presence of a C3592T and/or a G3602A mutation in exon 23 of the ALK gene according to SEQ ID NO:6 in thyroid sample of a patient, wherein the presence of either or both of the mutations indicates ATC and absence of either or both of the mutations indicates non-ATC.

25. The method of claim 24, wherein the thyroid sample is a fine needle aspirate (FNA).

26. The method of claim 24, wherein the thyroid sample is a tissue sample.

27. The method of claim 24, wherein the thyroid sample is a cytological sample.

28. The method of claim 24, further comprising providing a diagnosis based on the presence or absence of either or both of the mutations.

* * * * *